US009095305B2

(12) United States Patent
Engler et al.

(10) Patent No.: US 9,095,305 B2
(45) Date of Patent: *Aug. 4, 2015

(54) METHOD AND APPARATUS FOR INDICATING THE EMERGENCE OF A PRE-ULCER AND ITS PROGRESSION

(71) Applicant: Podimetrics, Inc., Cambridge, MA (US)

(72) Inventors: Jeffrey Mark Engler, Cambridge, MA (US); David Robert Linders, Somerville, MA (US); Jonathan David Bloom, Cambridge, MA (US); Brian Jude Petersen, Somerville, MA (US); Adam Geboff, San Jose, CA (US); David Charles Kale, Los Angeles, CA (US)

(73) Assignee: Podimetrics, Inc., Somerville, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/803,866

(22) Filed: Mar. 14, 2013

(65) Prior Publication Data

US 2013/0261496 A1  Oct. 3, 2013

Related U.S. Application Data

(63) Continuation of application No. 13/799,828, filed on Mar. 13, 2013.

(60) Provisional application No. 61/618,889, filed on Apr. 2, 2012.

(51) Int. Cl.
*A61B 5/00* (2006.01)
*A61B 5/01* (2006.01)

(52) U.S. Cl.
CPC .............. *A61B 5/447* (2013.01); *A61B 5/0022* (2013.01); *A61B 5/015* (2013.01); *A61B 5/7275* (2013.01); *A61B 5/0008* (2013.01); *A61B 2562/0276* (2013.01)

(58) Field of Classification Search
CPC ...... A61B 5/447; A61B 5/015; A61B 5/0022; A61B 5/7275; A61B 5/0008; A61B 2562/0276
USPC .................... 600/587, 592, 595, 549
See application file for complete search history.

(56) References Cited

U.S. PATENT DOCUMENTS

| 4,574,359 | A | 3/1986 | Ishizaka et al. ............... 364/557 |
| 4,592,000 | A | 5/1986 | Ishizaka et al. ............... 364/557 |

(Continued)

FOREIGN PATENT DOCUMENTS

| CN | 1308225 | 8/2001 | ............... G01K 3/00 |
| CN | 201312800 | 9/2009 | ............... A61B 5/00 |

(Continued)

OTHER PUBLICATIONS

Tamura et al. (Article entitled "A bed temperature monitoring system for assessing movement during sleep," Clin. Phys. Meas., 1988, vol. 9, No. 2, 139-145).*

(Continued)

*Primary Examiner* — Rene Towa
(74) *Attorney, Agent, or Firm* — Sunstein Kann Murphy & Timbers LLP

(57) ABSTRACT

A method of monitoring a patient's foot provides an open platform for receiving at least one foot. The platform has at least one temperature sensor for generating a plurality of temperature data values after receipt of the at least one foot. The method then forms a thermogram of the sole of the at least one foot from the temperature data, and determines whether the thermogram presents at least one of a plurality of prescribed patterns. Next, the method produces output information indicating the emergence of a pre-ulcer or progression of a known pre-ulcer in the at least one foot as a function of whether the thermogram is determined to present the at least one pattern.

29 Claims, 15 Drawing Sheets

(56) References Cited

U.S. PATENT DOCUMENTS

| | | | |
|---|---|---|---|
| 4,629,336 A | 12/1986 | Ishizaka | 374/169 |
| 4,647,918 A | 3/1987 | Goforth | 340/573 |
| 4,648,055 A | 3/1987 | Ishizaka et al. | 164/557 |
| 4,843,577 A | 6/1989 | Muramoto | 364/557 |
| 4,849,885 A * | 7/1989 | Stillwagon et al. | 600/549 |
| 4,866,621 A | 9/1989 | Ono | 364/413.03 |
| 4,878,184 A | 10/1989 | Okada et al. | 364/557 |
| 5,011,294 A | 4/1991 | Yamaguchi | 374/107 |
| 5,015,102 A | 5/1991 | Yamaguchi | 374/107 |
| 5,066,141 A | 11/1991 | Ikeda et al. | 374/169 |
| 5,259,389 A | 11/1993 | Muramoto et al. | 128/736 |
| 5,473,629 A | 12/1995 | Muramoto | 374/102 |
| 5,642,096 A | 6/1997 | Leyerer et al. | 340/573 |
| 5,678,566 A | 10/1997 | Dribbon | 128/779 |
| 5,929,332 A | 7/1999 | Brown | 73/172 |
| 6,090,050 A | 7/2000 | Constantinides | 600/549 |
| 6,195,921 B1 | 3/2001 | Truong | 36/136 |
| 6,398,740 B1 | 6/2002 | Lavery et al. | 600/549 |
| 6,767,330 B2 | 7/2004 | Lavery et al. | 600/549 |
| 6,807,869 B2 | 10/2004 | Farringdon et al. | 73/862.046 |
| 6,963,772 B2 | 11/2005 | Bloom et al. | 600/547 |
| 7,052,472 B1 | 5/2006 | Miller et al. | 600/549 |
| 7,167,734 B2 | 1/2007 | Khalil et al. | 600/310 |
| 7,206,718 B2 | 4/2007 | Cavanagh et al. | 702/155 |
| 7,318,004 B2 | 1/2008 | Butterfield | 702/130 |
| 7,637,657 B2 | 12/2009 | Yamamoto et al. | 374/169 |
| 7,716,005 B2 | 5/2010 | Shoureshi et al. | 702/131 |
| 7,726,206 B2 | 6/2010 | Terrafranca, Jr. et al. | 73/862.041 |
| 7,758,523 B2 | 7/2010 | Collings et al. | 600/592 |
| 8,360,987 B2 | 1/2013 | Kantro et al. | 600/549 |
| 2002/0082486 A1 | 6/2002 | Lavery et al. | 600/300 |
| 2002/0143257 A1* | 10/2002 | Newman et al. | 600/474 |
| 2005/0165284 A1* | 7/2005 | Gefen | 600/300 |
| 2006/0021261 A1 | 2/2006 | Face | 36/132 |
| 2006/0030783 A1 | 2/2006 | Tsai et al. | 600/549 |
| 2007/0038273 A1 | 2/2007 | Bales et al. | 607/88 |
| 2007/0039211 A1 | 2/2007 | Pichler | 36/140 |
| 2008/0214962 A1 | 9/2008 | Kantro et al. | 600/592 |
| 2008/0238660 A1* | 10/2008 | Dayton et al. | 340/539.14 |
| 2009/0219972 A1 | 9/2009 | Carlsson et al. | 374/107 |
| 2009/0306801 A1 | 12/2009 | Sivak et al. | 700/98 |
| 2010/0004566 A1 | 1/2010 | Son et al. | 600/592 |
| 2010/0041998 A1 | 2/2010 | Postel | 600/475 |
| 2010/0198022 A1 | 8/2010 | Vuillerme et al. | 600/301 |
| 2010/0268111 A1 | 10/2010 | Drinan et al. | 600/547 |
| 2010/0324455 A1 | 12/2010 | Rangel et al. | 600/592 |
| 2011/0015498 A1 | 1/2011 | Mestrovic et al. | 600/301 |
| 2011/0214501 A1 | 9/2011 | Ross et al. | 73/172 |
| 2011/0215930 A1* | 9/2011 | Lee et al. | 340/573.1 |
| 2011/0275956 A1 | 11/2011 | Son et al. | 600/592 |
| 2011/0313314 A1 | 12/2011 | Gefen | 600/555 |
| 2012/0109013 A1 | 5/2012 | Everett et al. | 600/587 |
| 2012/0190989 A1 | 7/2012 | Kaiser et al. | 600/476 |
| 2012/0221286 A1 | 8/2012 | Bisch et al. | 702/131 |
| 2013/0019503 A1 | 1/2013 | Vogt | 36/103 |

FOREIGN PATENT DOCUMENTS

| | | | |
|---|---|---|---|
| CN | 202263087 | 6/2012 | A61F 7/00 |
| DE | 202010013176 | 3/2011 | A61B 5/107 |
| EP | 0885587 | 12/1998 | A61B 5/00 |
| JP | 55071919 | 5/1980 | G01K 1/02 |
| JP | 2009539454 | 11/2009 | A61B 5/00 |
| KR | 101027367 | 4/2011 | A61B 5/145 |
| RU | 2433783 | 11/2011 | A61B 5/01 |
| WO | WO 2007/114768 | 10/2007 | G01K 11/12 |
| WO | WO 2008/058051 | 5/2008 | G01K 13/00 |
| WO | WO 2009/005373 | 1/2009 | A61B 5/01 |
| WO | WO 2010/021932 | 2/2010 | A61B 5/00 |
| WO | WO 2012/051394 | 4/2012 | G01N 21/00 |
| WO | WO 2012/084814 | 6/2012 | A43B 7/14 |

OTHER PUBLICATIONS

Bharara, M, Bharara, M—Pi—Technology Summary, 5 pages, undated.

Caselli, M.D. et al., "The Forefoot-to-Rearfoot Plantar Pressure Ratio Is Increased in Severe Diabetic Neuropathy and Can Predict Foot Ulceration," Diabetes Care, vol. 25, No. 6, pp. 1066-1071, Jun. 2002.

Dabiri et al., "Electronic Orthotics Shoe: Preventing Ulceration in Diabetics Patients," 30th Annual International IEEE EMBS Conference, pp. 771-774, Aug. 2008.

Kerstin Roback, "An overview of temperature monitoring devices for early detection of diabetic foot disorders," Linkoping University Post Print, 18 pages, undated.

Medgadget.com, "TempTouch for Foot Ulcer Detection," Xilas, Inc., 2 pages, Apr. 19, 2005.

Morley et al., "In-Shoe Multisensory Data Acquisition System," IEEE Transactions on Biomedical Engineering, vol. 48, No. 7, pp. 815-820, Jul. 2001.

Visual Footcare Technologies, LLC, "TempStat," Visual Footcare Technologies, LLC, Thermal Imagine Device, One unit: $125, 2 pages, undated.

Korean Intellectual Property Office, International Search Report—International Application No. PCT/US2013/030997, dated Jul. 8, 2013, together with the Written Opinion of the International Searching Authority, 13 pages.

Bharara et al., "Coming events cast their shadows before: detecting inflammation in the acute diabetic foot and the foot in remission," Diabetes/Metabolism Research and Reviews, vol. 28, pp. 15-20, 2012.

Brioschi et al., "Automated Computer Diagnosis of IR Medical Imaging," FLIR Technical Series, Application Note for Research & Science, FLIR Systems, Inc., 6 pages, 2011.

Chen et al., "Development of a Thermal and Hyperspectral Imaging System for Wound Characterization and Metabolic Correlation," John Hopkins Apl Technical Digest, vol. 26, No. 1, pp. 67-74, 2005.

Kaabouch et al., "Predicting neuropathic ulceration: analysis of static temperature distributions in thermal images," Journal of Biomedical Optics, vol. 15, No. 6, pp. 061715-1-061715-6, 2010.

Liu et al., "Infrared Dermal Thermography on Diabetic Feet Soles to Predict Ulcerations: a Case Study," Proc. of SPIE, vol. 8572, pp. 85720N-1-85720N-9, 2013.

Liu et al., "Statistical analysis of spectral data: a methodology for designing an intelligent monitoring system for the diabetic foot," Predicting neuropathic ulceration: analysis of static temperature distributions in thermal images, Journal of Biomedical Optics, vol. 18(12), pp. 126004-1-126004-11, Dec. 2013.

Van Netten et al., "Infrared Thermal Imaging for Automated Detection of Diabetic Foot Complications," Journal of Diabetes Science and Technology, vol. 7, Issue 5, pp. 1122-1129, Sep. 2013.

* cited by examiner

METHOD AND APPARATUS FOR INDICATING THE EMERGENCE OF A PRE-ULCER AND ITS PROGRESSION

PRIORITY

This patent application claims priority from provisional U.S. patent application No. 61/618,889, filed Apr. 2, 2012, entitled, "AUTONOMOUS METHOD FOR PREDICTING MEDICAL CONDITIONS IN MAMMALS," and naming Jonathan David Bloom, David Robert Linders, Jeffrey Mark Engler, David Charles Kale, and Adam Geboff as inventors, the disclosure of which is incorporated herein, in its entirety, by reference.

This patent application also is a continuation of U.S. patent application Ser. No. 13/799,828, filed Mar. 13, 2013, entitled, "METHOD AND APPARATUS FOR INDICATING THE RISK OF AN EMERGING ULCER," and naming Jonathan David Bloom, David Robert Linders, Jeffrey Mark Engler, Brian Petersen, David Charles Kale, and Adam Geboff as inventors, the disclosure of which is incorporated herein, in its entirety, by reference.

RELATED APPLICATION

This patent application is related to the following utility patent application, which is incorporated herein, in its entirety, by reference:

1. U.S. patent application Ser. No. 13/799,847, filed on Mar. 13, 2013, entitled, "METHOD AND APPARATUS FOR INDICATING THE EMERGENCE OF AN ULCER," and naming Jonathan David Bloom, David Robert Linders, Jeffrey Mark Engler, Brian Petersen, David Charles Kale, and Adam Geboff as inventors.

FIELD OF THE INVENTION

The invention generally relates to ulcers on living beings and, more particularly, the invention relates to evaluating portions of living beings for ulcers.

BACKGROUND OF THE INVENTION

Open sores on an external surface of the body often form septic breeding grounds for infection, which can lead to serious health complications. For example, foot ulcers on the bottom of a diabetic's foot can lead to gangrene, leg amputation, or, in extreme cases, death. The healthcare establishment therefore recommends monitoring a diabetic's foot on a regular basis to avoid these and other dangerous consequences. Unfortunately, known techniques for monitoring foot ulcers, among other types of ulcers, often are inconvenient to use, unreliable, or inaccurate, thus reducing compliance by the very patient populations that need it the most.

SUMMARY OF VARIOUS EMBODIMENTS

In accordance with one embodiment of the invention, a method of monitoring a patient's foot provides an open platform for receiving at least one foot. The platform has at least one temperature sensor for generating a plurality of temperature data values after receipt of the at least one foot. The method then forms a thermogram of the sole of the at least one foot from the temperature data, and determines whether the thermogram presents at least one of a plurality of prescribed patterns. Next, the method produces output information indicating the emergence of a pre-ulcer or progression of a known pre-ulcer in the at least one foot as a function of whether the thermogram is determined to present the at least one pattern.

The method also may detect a prescribed pattern on a portion of the at least one foot indicating the presence of a pre-ulcer on the portion, and then compare the portion of the at least one foot with data from a previous thermogram of the portion of the same foot. The previous thermogram may indicate that the portion of the at least one foot is pre-ulcer free. In addition, the method may detect a prescribed pattern on a portion of the at least one foot indicating the presence of a given pre-ulcer on the portion, and then compare the portion of the at least one foot with data from a previous thermogram of the portion of the same foot—e.g., to determine whether the given pre-ulcer has changed. In this instance, the previous thermogram may indicate the presence of the given pre-ulcer in that the portion of the at least one foot.

In illustrative embodiments, the plurality of temperature sensors are at discrete locations on the foot. In that case, the method may form the thermogram by interpolating temperature data between at least two of the plurality of temperature sensors to produce approximate temperature readings at locations between the sensors.

The platform may have a receiving area for receiving the at least one foot, and/or for positioning both feet. The receiving area has a surface area that is greater than the surface area of the at least one foot. Accordingly, the thermogram can have data for substantially the entirety of the sole. In addition, unlike isotherms, the thermogram typically is expected to have data showing substantially continuous two-dimensional spatial temperature variations across portions of the at least one foot.

To indicate the emergence of a pre-ulcer or progression of a known pre-ulcer, the method may use any of a number of different patterns. One shows a deviation in two portions of the same foot, while a second shows a deviation in corresponding portions of the patient's two feet. Another pattern shows a deviation in one portion of the same foot over time. The deviation may be a temperature deviation (e.g., about 4 degrees F.) at or across the specified foot geography.

In addition to having any of a variety of different form factors (e.g., similar to a floor mat or a bathroom scale), the open platform often does not necessarily visually display the thermogram. Instead, its data often is used to indicate the emergence of a pre-ulcer (or monitor a pre-ulcer) without the need to display the thermogram. Moreover, some embodiments determine the orientation of the at least one foot to produce orientation information, and then use that orientation information to determine whether the thermogram presents at least one of a plurality of prescribed patterns.

Some embodiments forward, across a network, a data message having the temperature data representing the thermogram. In response, some embodiments may receive a risk message, also from the network, having the output information. Among other things, output information may include information for displaying quantitative indicia indicating the risk of an ulcer emerging.

The plurality of temperature sensors may include a plurality of stationary sensors and/or at least one contact sensor. Moreover, in addition to indicating the emergence of a pre-ulcer or progression of a known pre-ulcer, some embodiments produce additional output information indicating the risk of an ulcer emerging on the foot, also as a function of whether the thermogram is determined to present the at least one prescribed pattern.

In accordance with another embodiment of the invention, a method of monitoring a patient's foot receives a thermogram message through a network from an open platform for receiving at least one foot. The open platform has at least one temperature sensor for generating a plurality of temperature data values after receipt of the at least one foot. The thermogram message has the temperature data values. The method forms a thermogram of the sole of the at least one foot from the temperature data, determines whether the thermogram presents at least one of a plurality of prescribed patterns, and produces output information indicating the emergence of a pre-ulcer or progression of a known pre-ulcer in the at least one foot as a function of whether the thermogram is determined to present the at least one pattern.

In accordance with other embodiments of the invention, an apparatus for monitoring a patient's foot has an input for receiving a thermogram message through a network from an open platform for receiving at least one foot. The open platform has at least one temperature sensor for generating a plurality of temperature data values after receipt of the at least one foot. The thermogram message has the temperature data values. The apparatus also has a thermogram generator (operatively coupled with the input) configured to produce a thermogram of the sole of the at least one foot from the temperature data, and, a pattern recognition system (operatively coupled with the thermogram generator) configured to determine whether the thermogram presents at least one of a plurality of prescribed patterns. The apparatus further includes an analyzer (operatively coupled with the pattern recognition system) configured to produce output information indicating the emergence of a pre-ulcer or progression of a known pre-ulcer in the at least one foot as a function of whether the thermogram is determined to present the at least one pattern.

Illustrative embodiments of the invention are implemented as a computer program product having a computer usable medium with computer readable program code thereon. The computer readable code may be read and utilized by a computer system in accordance with conventional processes.

BRIEF DESCRIPTION OF THE DRAWINGS

Those skilled in the art should more fully appreciate advantages of various embodiments of the invention from the following "Description of Illustrative Embodiments," discussed with reference to the drawings summarized immediately below.

DESCRIPTION OF ILLUSTRATIVE EMBODIMENTS

In illustrative embodiments, a method and apparatus analyze a patient's foot 1) to determine if there is a new pre-ulcer emerging in the foot, or 2) to track the progression of a known pre-ulcer in the foot. This permits patients, their healthcare providers, and/or their caregivers to intervene earlier, reducing the risk of more serious complications. To that end, an open platform receives the patient's foot and generates temperature data that is processed to form a thermogram. If the thermogram presents at least one of a number of prescribed patterns, then various embodiments produce output information for indicating pre-ulcer emergence or for tracking known pre-ulcers. Details of illustrative embodiments are discussed below.

Figure 1:
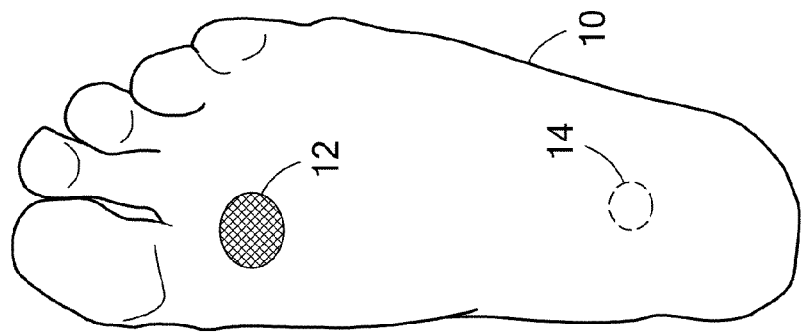
FIG. 1 schematically shows a foot having a prominent foot ulcer and a pre-ulcer.

FIG. 1 schematically shows a bottom view of a patient's foot 10 that, undesirably, has an ulcer 12 and a pre-ulcer 14 (described below and shown in phantom since pre-ulcers 14 do not break through the skin). As one would expect, an ulcer 12 on this part of the foot 10 typically is referred to as a "foot ulcer 12." Generally speaking, an ulcer is an open sore on a surface of the body generally caused by a breakdown in the skin or mucous membrane. Diabetics often develop foot ulcers 12 on the soles of their feet 10 as part of their disease. In this setting, foot ulcers 12 often begin as a localized inflammation that may progress to skin breakdown and infection.

It should be noted that discussion of diabetes and diabetics is but one example and used here simply for illustrative purposes only. Accordingly, various embodiments apply to other types of diseases (e.g., stroke, deconditioning, sepsis, friction, coma, etc. . . . ) and other types of ulcers—such embodiments may apply generally where there is a compression or friction on the living being's body over an extended period of time. For example, various embodiments also apply to ulcers formed on different parts of the body, such as on the back (e.g., bedsores), inside of prosthetic sockets, or on the buttocks (e.g., a patient in a wheel chair). Moreover, illustrative embodiments apply to other types of living beings beyond human beings, such as other mammals (e.g., horses or dogs). Accordingly, discussion of diabetic human patients having foot ulcers 12 is for simplicity only and not intended to limit all embodiments of the invention.

Many prior art ulcer detection technologies known to the inventors suffered from one significant problem—patient compliance. If a diseased or susceptible patient does not regularly check his/her feet 10, then that person may not learn of an ulcer 12 or a pre-ulcer 14 until it has emerged through the skin and/or requires significant medical treatment. Accordingly, illustrative embodiments implement an ulcer monitoring system in any of a variety of forms—preferably in an easy to use form factor that facilitates and encourages regular use.

Figure 2A:
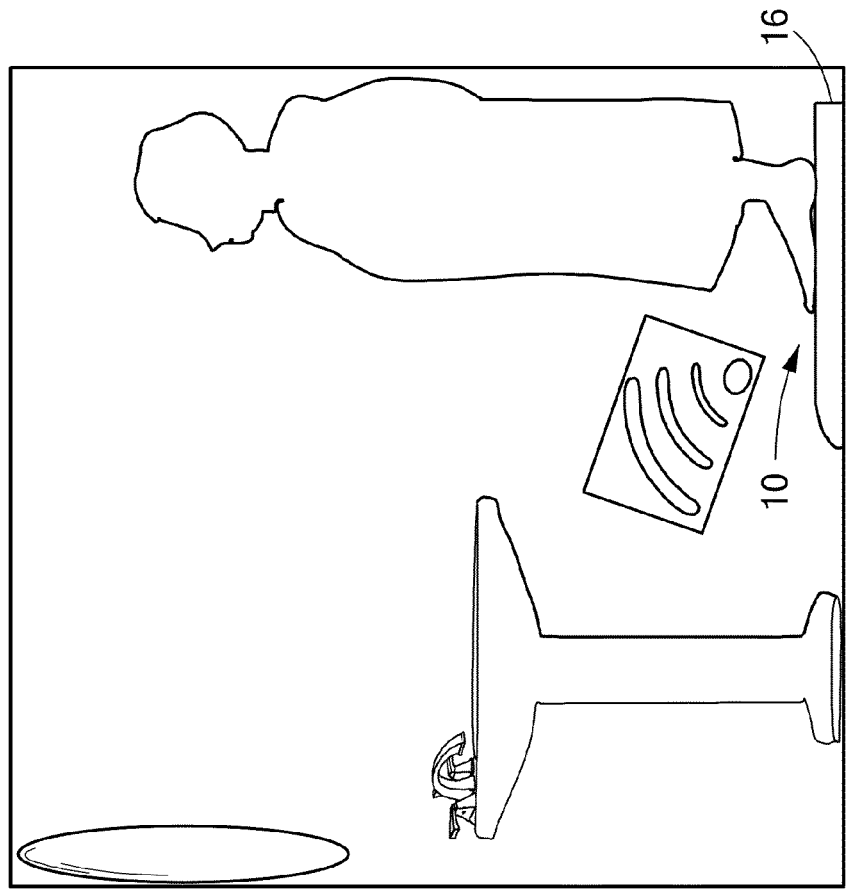
FIG. 2A schematically shows one use and form factor that may be implemented in accordance with illustrative embodiments of the invention.
Figure 2B:
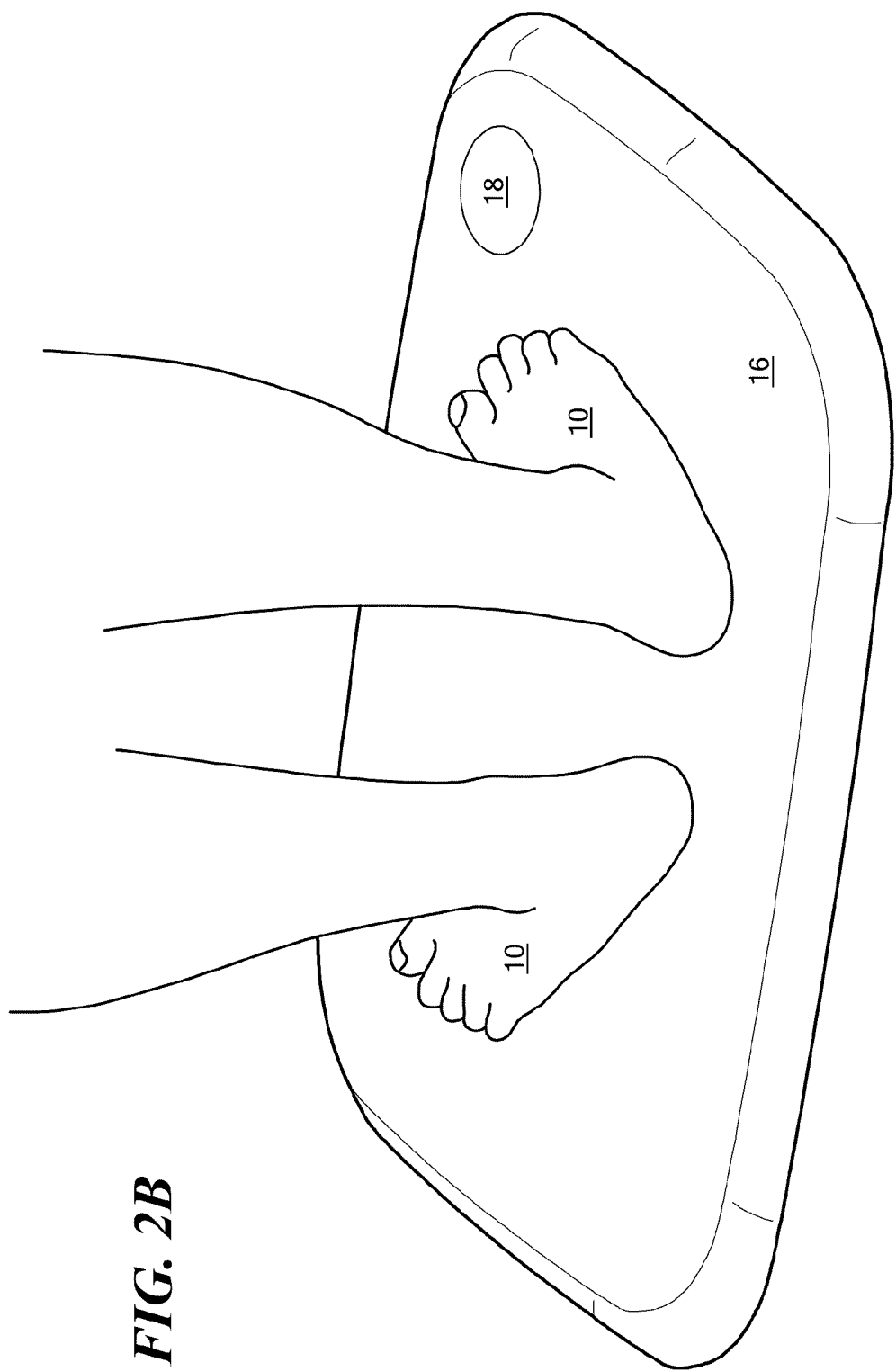
FIG. 2B schematically shows an open platform that may be configured in accordance with illustrative embodiments of the invention.

FIGS. 2A and 2B schematically show one form factor, in which a patient/user steps on an open platform 16 that gathers data about that user's feet 10. In this particular example, the open platform 16 is in the form of a floor mat placed in a location where he the patient regularly stands, such as in front of a bathroom sink, next to a bed, in front of a shower, on a footrest, or integrated into a mattress. As an open platform 16, the patient simply may step on the top sensing surface of the platform 16 to initiate the process. Accordingly, this and other form factors favorably do not require that the patient affirmatively decide to interact with the platform 16. Instead, many expected form factors are configured to be used in areas where the patient frequently stands during the course of their day without a foot covering. Alternatively, the open platform 16 may be moved to directly contact the feet 10 of a patient that cannot stand. For example, if the patient is bedridden, then the platform 16 may be brought into contact with the patient's feet 10 while in bed.

A bathroom mat or rug are but two of a wide variety of different potential form factors. Others may include a platform 16 resembling a scale, a stand, a footrest, a console, a tile built into the floor, or a more portable mechanism that receives at least one of the feet 10. The implementation shown in FIGS. 2A and 2B has a top surface area that is larger than the surface area of one or both of the feet 10 of the patient. This enables a caregiver to obtain a complete view of the patient's entire sole, providing a more complete view of the foot 10.

The open platform 16 also has some indicia or display 18 on its top surface they can have any of a number of functions. For example, the indicia can turn a different color or sound an alarm after the readings are complete, show the progression of the process, or display results of the process. Of course, the indicia or display 18 can be at any location other than on the top surface of the open platform 16, such as on the side, or a separate component that communicates with the open platform 16. In fact, in addition to, or instead of, using visual or audible indicia, the platform 16 may have other types of indicia, such as tactile indicia/feedback, our thermal indicia.

Rather than using an open platform 16, alternative embodiments may be implemented as a closed platform 16, such as a shoe or sock that can be regularly worn by a patient, or worn on an as-needed basis. For example, the insole of the patient's shoe or boot may have the functionality for detecting the emergence of a pre-ulcer 14 or ulcer 12, and/or monitoring a pre-ulcer 14 or ulcer 12.

Figure 3A:
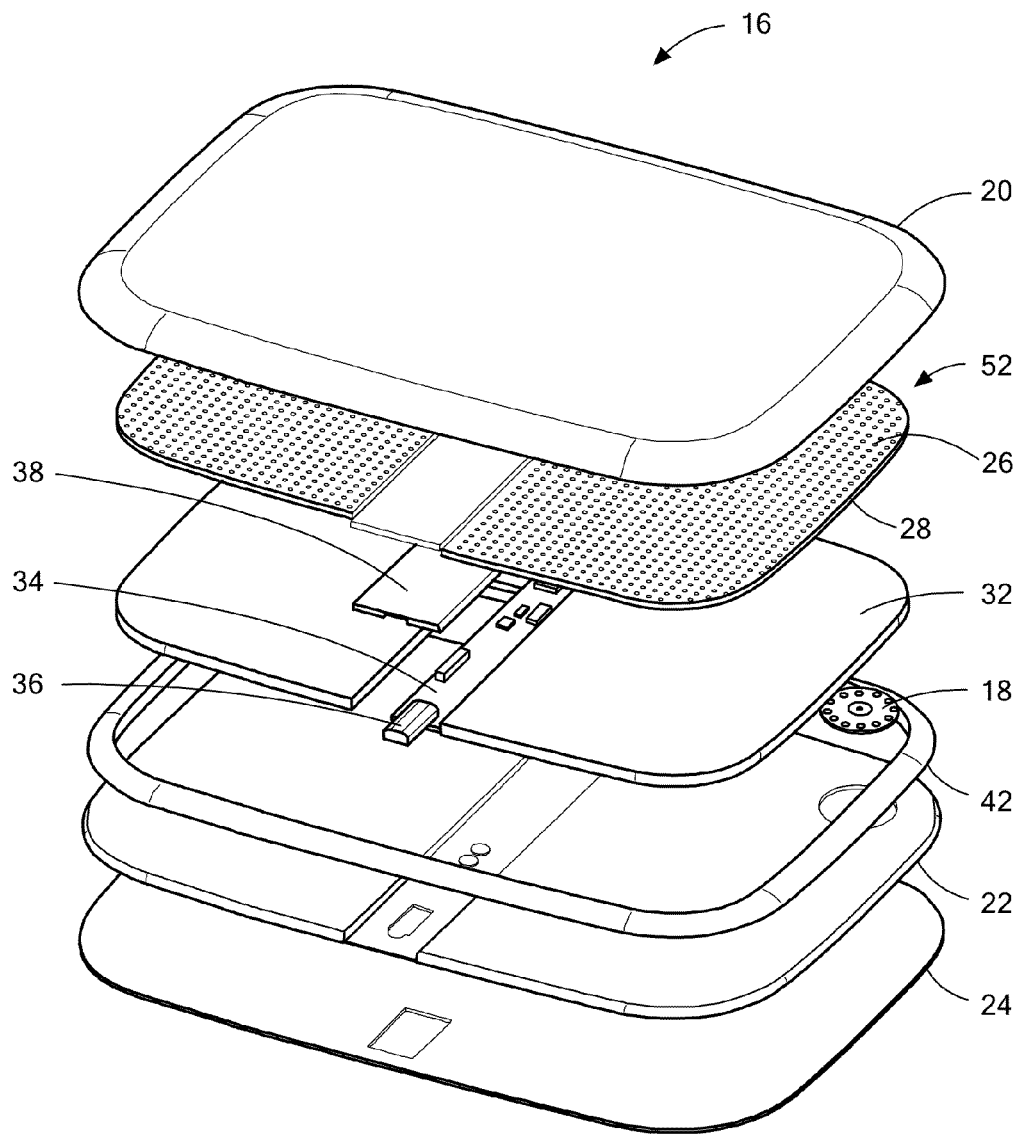
FIG. 3A schematically shows an exploded view of one type of open platform that may be configured in accordance with illustrative embodiments of the invention.

To monitor the health of the patient's foot (discussed in greater detail below), the platform 16 of FIGS. 2A and 2B gathers temperature data about a plurality of different locations on the sole of the foot 10. This temperature data provides the core information ultimately used to determine the health of the foot 10. FIG. 3 schematically shows an exploded view of the open platform 16 configured and arranged in accordance with one embodiment of the invention. Of course, this embodiment is but one of a number of potential implementation and, like other features, is discussed by example only.

As shown, the platform 16 is formed as a stack of functional layers sandwiched between a cover 20 and a rigid base 22. For safety purposes, the base preferably has rubberized or has other non-skid features on its bottom side. FIG. 3 shows one embodiment of this non-skid feature as a non-skid base 24. The platform 16 preferably has relatively thin profile to avoid tripping the patient and making it easy to use.

To measure foot temperature, the platform 16 has an array or matrix of temperature sensors 26 fixed in place directly underneath the cover 20. More specifically, the temperature sensors 26 are positioned on a relatively large printed circuit board 28. The sensors 26 preferably are laid out in a two-dimensional array/matrix of stationary contact sensors on the printed circuit board 28. The pitch or distance between the preferably is relatively small, thus permitting more temperature sensors 26 on the array. Among other things, the temperature sensors 26 may include temperature sensitive resistors (e.g., printed or discrete components mounted onto the circuit board 28), thermocouples, fiberoptic temperature sensors, or a thermochromic film. Accordingly, when used with temperature sensors 26 that require direct contact, illustrative embodiments form the cover 20 with a thin material having a relatively high thermal conductivity. The platform 16 also may use temperature sensors 26 that can still detect temperature through a patient's socks.

Other embodiments may use noncontact temperature sensors 26, such as infrared detectors. Indeed, in that case, the cover 20 may have openings to provide a line of sight from the sensors 26 to the sole of the foot 10. Accordingly, discussion of contact sensors is by example only and not intended to limit various embodiments. As discussed in greater detail below and noted above, regardless of their specific type, the plurality of sensors 26 generate a plurality of corresponding temperature data values for a plurality of portions/spots on the patient's foot 10 to monitor the health of the foot 10.

Some embodiments also may use pressure sensors for various functions, such as to determine the orientation of the feet 10 and/or to automatically begin the measurement process. Among other things, the pressure sensors may include piezoelectric, resistive, capacitive, or fiber-optic pressure sensors. This layer of the platform 16 also may have additional sensor modalities beyond temperature sensors 26 and pressure sensors, such as positioning sensors, GPS sensors, accelerometers, gyroscopes, and others known by those skilled in the art.

Figure 3B:
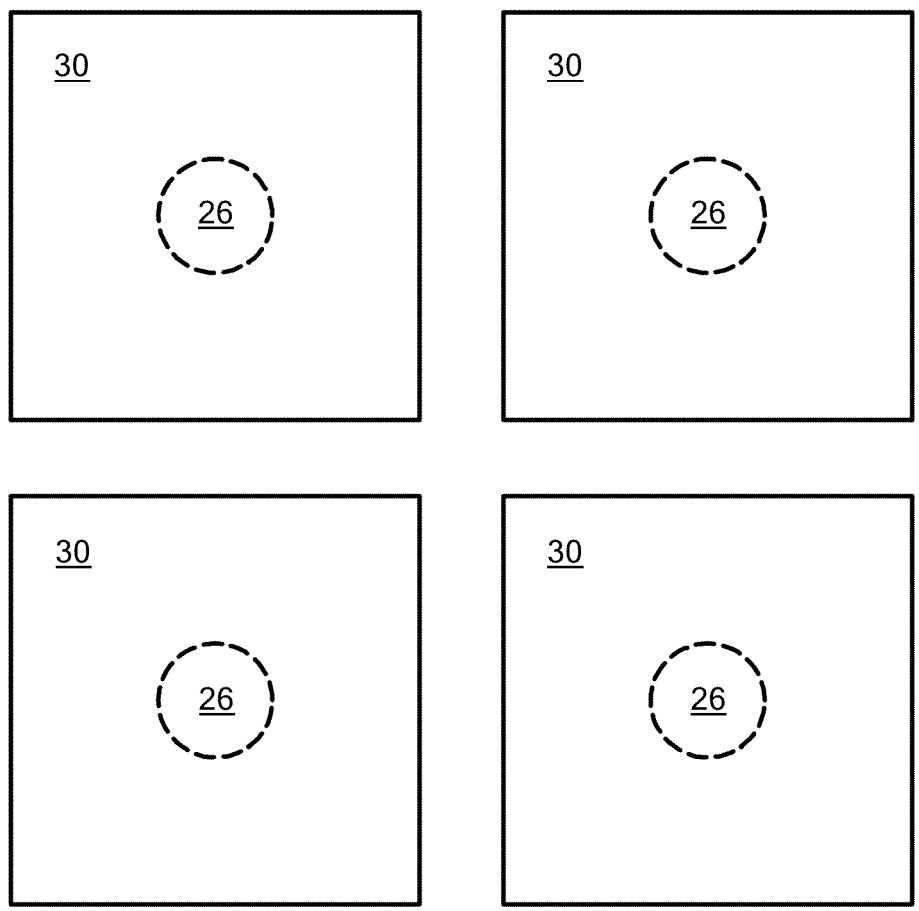
FIG. 3B schematically shows a close up view of the platform with details of the pads and temperature sensors.

To reduce the time required to sense the temperature at specific points, illustrative embodiments position an array of heat conducting pads 30 over the array of temperature sensors 26. To illustrate this, FIG. 3B schematically shows a small portion of the array of temperature sensors 26 showing four temperature sensors 26 and their pads 30. The temperature sensors 26 are drawn in phantom because they preferably are covered by the pads 30. Some embodiments do not cover the sensors 26, however, and simply thermally connect the sensors 26 with the pads 26.

Accordingly, each temperature sensor 26 has an associated heat conducting pad 30 that channels heat from one two dimensional portion of the foot 10 (considered a two dimensional area although the foot may have some depth dimensionality) directly to its exposed surface. The array of conducting pads 30 preferably takes up the substantial majority of the total surface area of the printed circuit board 28. The distance between the pads 30 thermally isolates them from one another, thus eliminating thermal short-circuits.

For example, each pad 30 may have a square shape with each side having a length of between about 0.1 and 1.0 inches. The pitch between pads 30 thus is less than that amount. Accordingly, as a further detailed example, some embodiments may space the temperature sensors 26 about 0.4 inches apart with 0.25 inch (per side) square pads 30 oriented so that each sensor 26 is at the center of the square pads 30. This leaves an open region (i.e., a pitch) of about 0.15 inches between the square pads 30. Among other things, the pads 30 may be formed from a film of thermally conductive metal, such as a copper.

As suggested above, some embodiments do not use an array of temperature sensors 26. Instead, such embodiments may use a single temperature sensor 26 that can obtain a temperature reading of most or all of the sole. For example, a single sheet of a heat reactive material, such as a thermochromic film (noted above), or similar apparatus should suffice. As known by those in the art, a thermochromic film, based on liquid crystal technology, has internal liquid crystals that reorient to produce an apparent change in color in response to a temperature change, typically above the ambient temperature. Alternatively, one or more individual temperature sensors 26, such as thermocouples or temperature sensor resistors, may be movable to take repeated temperature readings across the bottom of the foot 10.

To operate efficiently, the open platform 16 should be configured so that its top surface contacts substantially the entire sole of the patient's foot 10. To that end, the platform 16 has a flexible and movable layer of foam 32 or other material that conforms to the user's foot 10. For example, this layer should conform to the arch of the foot 10. Of course, the sensors 26, printed circuit board 28, and cover 20 also should be similarly flexible and yet robust to conform to the foot 10 in a corresponding manner. Accordingly, the printed circuit board 28 preferably is formed largely from a flexible material that supports the circuit. For example, the printed circuit board 28 may be formed primarily from a flex circuit that supports the temperature sensors 26, or it may be formed from strips of material that individually flex when receiving feet. Alternative embodiments may not have such flexibility (e.g., formed from conventional printed circuit board material, such as FR-4) and thus, produce less effective data.

The rigid base 22 positioned between the foam 32 and the non-skid base 24 provides rigidity to the overall structure. In addition, the rigid base 22 is contoured to receive a motherboard 34, a battery pack 36, a circuit housing 38, and additional circuit components that provide further functionality. For example, the motherboard 34 may contain integrated circuits and microprocessors that control the functionality of the platform 16.

In addition, the motherboard 34 also may have a user interface/indicia display 18 as discussed above, and a communication interface 40 (FIG. 5) to connect to a larger network 44, such as the Internet. The communication interface 40 may connect wirelessly or through a wired connection with the larger network 44, implementing any of a variety of different data communication protocols, such as Ethernet. Alternatively, the communication interface 40 can communicate through an embedded Bluetooth or other short range wireless radio that communicates with a cellular telephone network 44 (e.g., a 3G or 4G network).

The platform 16 also may have edging 42 and other surface features that improve its aesthetic appearance and feel to the patient. The layers may be secured together using one or more of an adhesive, snaps, nuts, bolts, or other fastening devices.

Figure 4:
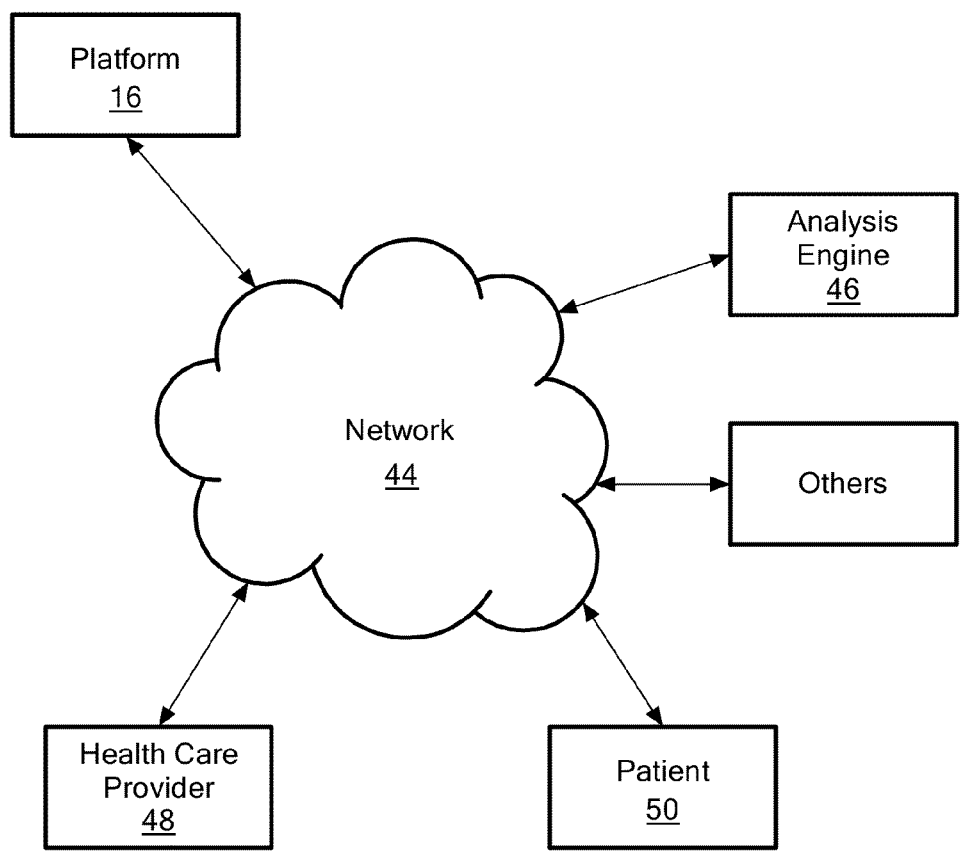
FIG. 4 schematically shows a network implementing of illustrative embodiments of the invention.

Although it gathers temperature and other data about the patient's foot, illustrative embodiments may locate additional logic for monitoring foot health at another location. For example, such additional logic may be on a remote computing device. To that and other ends, FIG. 4 schematically shows one way in which the platform 16 can communicate with a larger data network 44 in accordance with various embodiments the invention. As shown, the platform 16 may connect with the Internet through a local router, through its local area network, or directly without an intervening device. This larger data network 44 (e.g., the Internet) can include any of a number of different endpoints that also are interconnected. For example, the platform 16 may communicate with an analysis engine 46 that analyzes the thermal data from the platform 16 and determines the health of the patient's foot 10. The platform 16 also may communicate directly with a healthcare provider 48, such as a doctor, nurse, relative, and/or organization charged with managing the patient's care. In fact, the platform 16 also can communicate with the patient, such as through text message, telephone call, e-mail communication, or other modalities as the system permits.

Figure 5:
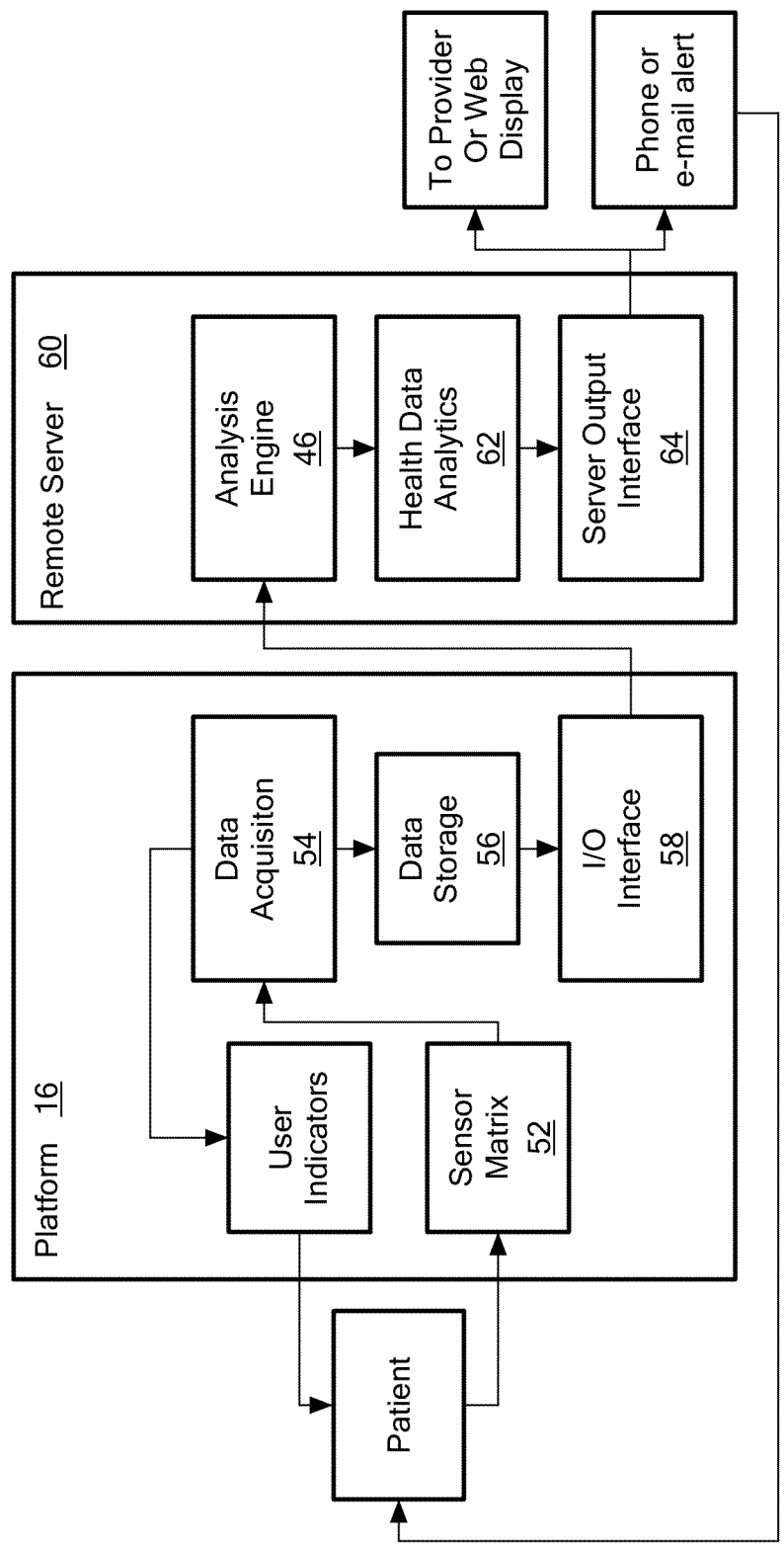
FIG. 5 schematically shows an overview of various components of illustrative embodiments of the invention.

FIG. 5 schematically shows a block diagram of a foot monitoring system, showing the platform 16 and the network 44 with its interconnected components in more detail. As shown, the patient communicates with the platform 16 by standing on or being received in some manner by the array of sensors 26, which is represented in this figure as a "sensor matrix 52." A data acquisition block 54, implemented by, for example, the motherboard 34 and circuitry shown in FIG. 3, controls acquisition of the temperature and other data for storage in a data storage device 56. Among other things, the data storage device 56 can be a volatile or nonvolatile storage medium, such as a hard drive, high-speed random-access-memory ("RAM"), or solid-state memory. The input/output interface port 40, also controlled by the motherboard 34 and other electronics on the platform 16, selectively transmits or forwards the acquired data from the storage device to the analysis engine 46 on a remote computing device, such as a server 60. The data acquisition block 54 also may control the user indicators/displays 18, which provide feedback to the user through the above mentioned indicia (e.g., audible, visual, or tactile).

As noted above and discussed in greater detail below with regard to FIGS. 7 and 8, the analysis engine 46, on the remote server 60, analyzes the data received from the platform 16 in conjunction with a health data analytics module 62. A server output interface 64 forwards the processed output information/data from the analysis engine 46 and health data analytics module 62 toward others across the network 44, such as to a provider, a web display, or to the user via a phone, e-mail alert, text alert, or other similar way.

This output message may have the output information in its relatively raw form for further processing. Alternatively, this output message may have the output information formatted in a high-level manner for easy review by automated logic or a person viewing the data. Among other things, the output message may indicate the actual emergence of an ulcer 12 or a pre-ulcer 14, the risk of the emergence of an ulcer 12 or a pre-ulcer 14, or simply that the foot 10 is healthy and has no risks of ulcer 12 or pre-ulcer 14. In addition, this output message also may have information that helps an end-user or healthcare provider 48 monitor an ulcer 12 or pre-ulcer 14.

Using a distributed processing arrangement like that shown in FIG. 5 has a number of benefits. Among other things, it permits the platform 16 to have relatively simple and inexpensive components that are unobtrusive to the patient. Moreover, this permits a "software-as-a-service" business model ("SAAS model"), which, among other things, permits more flexibility in the functionality, typically easier patient monitoring, and more rapid functional updates. In addition, the SAAS model facilitates accumulation of patient data to improve analytic capability.

Some embodiments may distribute and physically position the functional components in a different manner. For example, the platform 16 may have the analysis engine 46 on its local motherboard 34. In fact, some embodiments provide the functionality entirely on the platform 16 and/or within other components in the local vicinity of the platform 16. For example, all of those functional elements (e.g., the analysis engine 46 and other functional elements) may be within the housing formed by the cover 20 and the rigid base 22. Accordingly, discussion of a distributed platform 16 is but one of a number of embodiments that can be adapted for a specific application or use.

Figure 6:
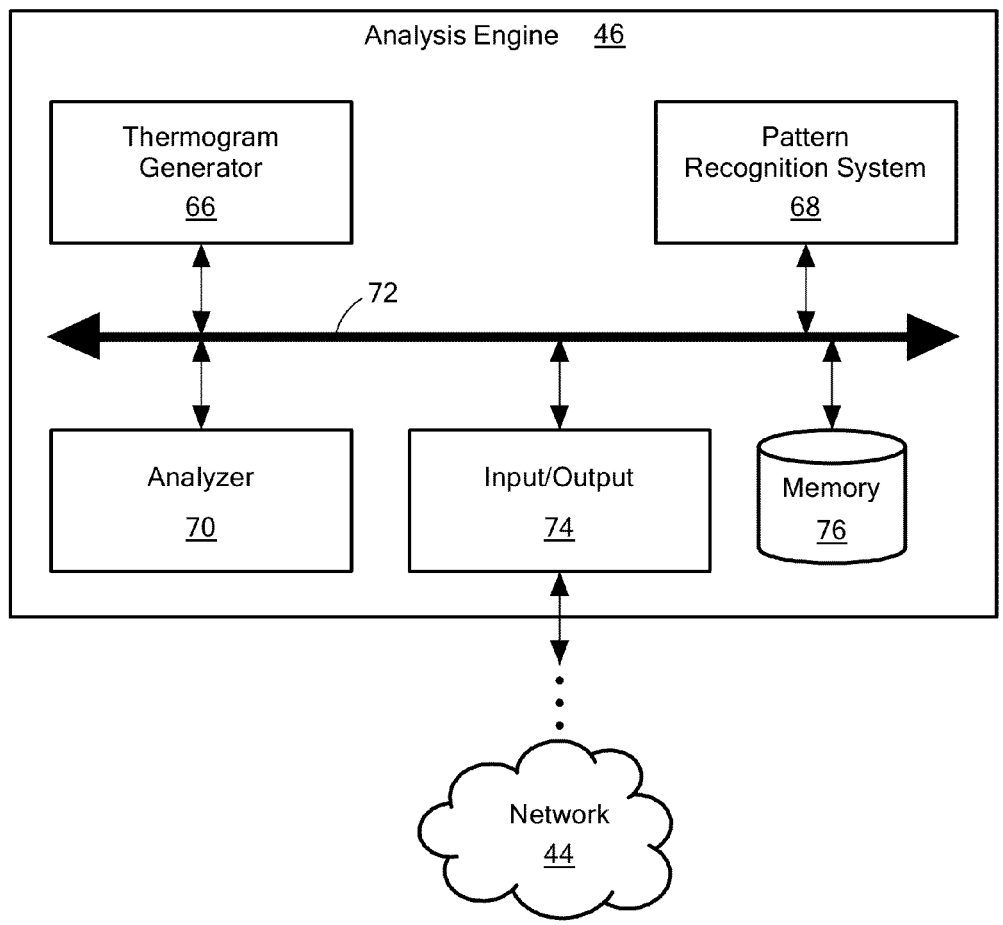
FIG. 6 schematically shows details of a data processing module in accordance with illustrative embodiments of the invention.

Those skilled in the art can perform the functions of the analysis engine 46 using any of a number of different hardware, software, firmware, or other non-known technologies. FIG. 6 shows several functional blocks that, with other functional blocks, may be configured to perform the functions of the analysis engine 46. This figure simply shows the blocks and is illustrative of one way of implementing various embodiments, while FIGS. 7 and 8 describe their functions in greater detail.

In summary, the analysis engine 46 of FIG. 6 has a thermogram generator 66 configured to form a thermogram of the patient's foot 10 or feet 10 based on a plurality of temperature readings from the bottom of the foot 10, and a pattern recognition system 68 configured to determine whether the thermogram presents any of a number of different prescribed patterns. Pattern data and other information may be stored in a local memory 76. As discussed below, if the thermogram presents any of these prescribed patterns, then the foot 10 may be unhealthy in some manner (e.g., having a pre-ulcer 14 or an ulcer 12).

The analysis engine 46 also has an analyzer 70 configured to produce the above noted output information, which indicates any of a number of different conditions of the foot 10. For example, the output information may indicate the risk that an ulcer 12 will emerge, the emergence of a pre-ulcer 14 (i.e., the first indication of a pre-ulcer 14), the progression of a known ulcer 12, or the emergence of a new ulcer 12 (i.e., the first indication of any given ulcer 12 to the patient and associated support). Communicating through some interconnect mechanism, such as a bus 72 or network connection, these modules cooperate to determine the status of the foot 10, which may be transmitted or forwarded through an input/output port 74 that communicates with the prior noted parties across the larger data network 44.

Figure 7:
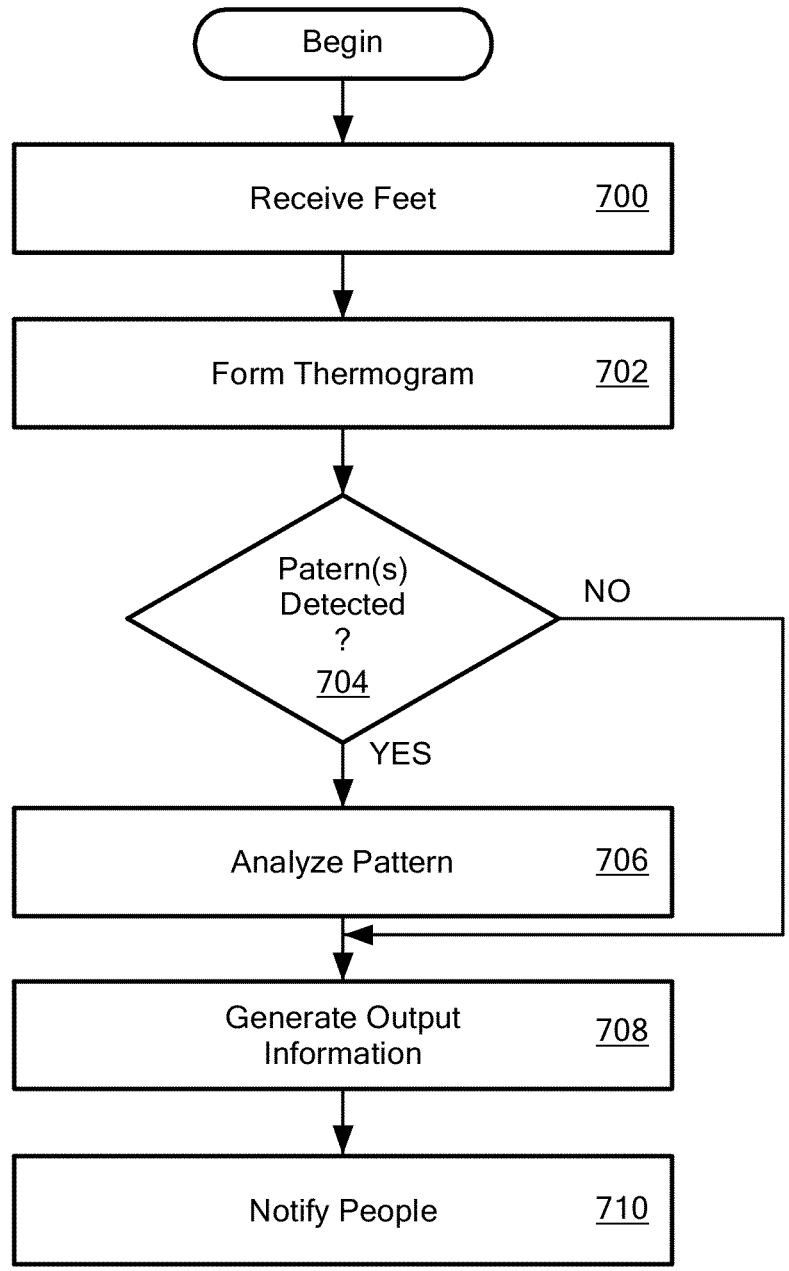
FIG. 7 shows a process of monitoring the health of the patient's foot or feet in accordance with illustrative embodiments the invention.

FIG. 7 shows a process that uses the various components described above in FIGS. 1 through 6 to determine the health of the patient's foot 10. It should be noted that this process is a simplified, high level summary of a much larger process and thus, should not be construed to suggest that only these steps are required. In addition, some of the steps may be performed in a different order than those described below. Although functions and processes of this process are described as being executed by the functional blocks in FIGS. 5 and 6, some embodiments can be executed by other functional components.

The process begins at step 700, in which the platform 16 receives the patient's feet 10 on its top surface, which may be considered a foot receiving area. For example, as shown in FIG. 2A, the patient may step on the open platform 16 in front of the bathroom sink while washing her hands, brushing her teeth, or performing some other routine, frequent daily task. Presumably, the platform 16 is energized before the patient steps onto it. Some embodiments, however, may require that the platform 16 be affirmatively energized by the patient turning on power in some manner (e.g., actuating a power switch). Other embodiments, however, normally may operate in a low power, conservation mode (a "sleep mode") that rapidly turns on in response to a stimulus, such as receipt of the patient's feet 10.

Accordingly, the platform 16 controls the sensor array to measure the temperature at the prescribed portions of the patient's foot/sole. At the same time, the user indicator display 18 may deliver affirmative feedback to the patient by any of the above discussed ways. After the patient steps on the platform 16, the temperature sensors 26 may take a relatively long time to ultimately make their readings. For example, this process can take between 30 to 60 seconds. Many people, however, do not have that kind of patience and thus, may step off the platform 16 before it has completed its analysis. This undesirably can lead to inaccurate readings. In addition, these seemingly long delay times can reduce compliance.

The inventors recognized these problems. Accordingly, illustrative embodiments of the invention do not require such long data acquisition periods. Instead, the system can use conventional techniques to extrapolate a smaller amount of real temperature data (e.g., a sparer set of the temperature data) to arrive at an approximation of the final temperature at each point of the foot. For example, this embodiment may use techniques similar to those used in high speed thermometers to extrapolate the final temperature data using only one to three seconds of actual temperature data.

Figure 9A:
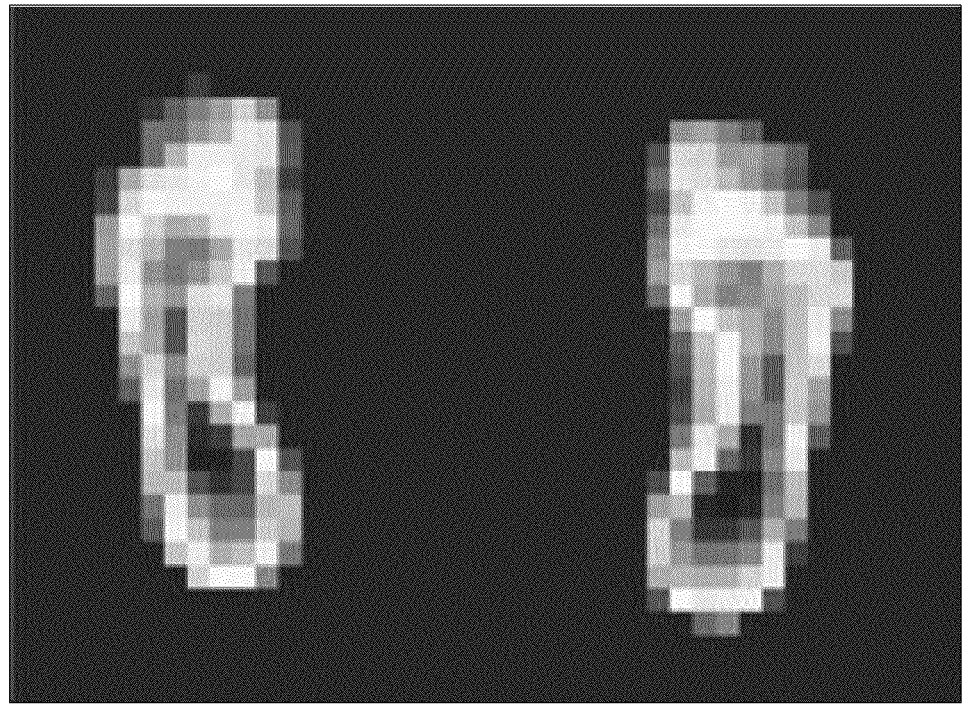
FIGS. 9A-9D schematically show the progression of the thermogram and how it is processed in accordance with one embodiment of the invention.

This step therefore produces a matrix of discrete temperature values across the foot 10 or feet 10. FIG. 9A graphically shows one example of this discrete temperature data for two feet 10. As discrete temperature values, this representation does not have temperature information for the regions of the foot 10 between the temperature sensors 26. Accordingly, using this discrete temperature data as shown in FIG. 9A, the process forms a thermogram of the foot 10 or feet 10 under examination (step 702).

In simple terms, as known by those in the art, a thermogram is a data record made by a thermograph, or a visual display of that data record. A thermograph simply is an instrument that records temperatures (i.e., the platform 16). As applied to illustrative embodiments, a thermograph measures temperatures and generates a thermogram, which is data, or a visual representation of that data, of the continuous two-dimensional temperature data across some physical region, such as a foot 10. Accordingly, unlike an isothermal representation of temperature data, a thermogram provides a complete, continuous data set/map of the temperatures across an entire two-dimensional region/geography. More specifically, in various embodiments, a thermogram shows (within accepted tolerances) substantially complete and continuous two-dimensional spatial temperature variations and gradients across portions of the sole of (at least) a single foot 10, or across the entire sole of the single foot 10.

Figure 8:
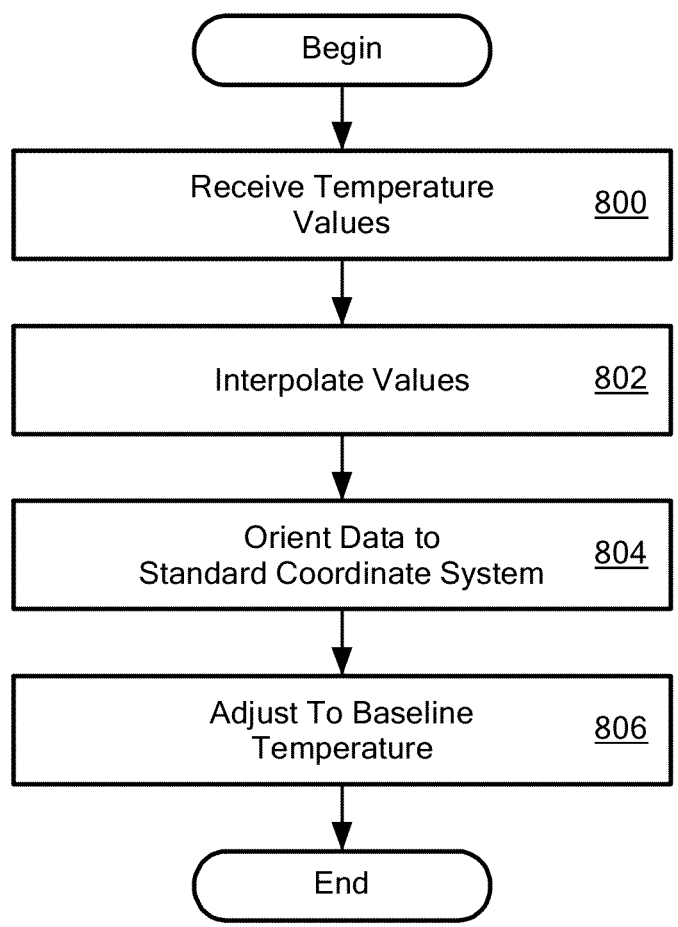
FIG. 8 shows a process of forming a thermogram in accordance with illustrative embodiments of the invention.

Momentarily turning away from FIG. 7, FIG. 8 shows a process that step 702 uses to form a thermogram. This discussion will return to FIG. 7 and proceed from step 702 after completing the thermogram formation process of FIG. 8. It should be noted that, in a manner similar to FIG. 7, the process of FIG. 8 is a simplified, high level summary of a larger process and thus, should not be construed to suggest that only these steps are required. In addition, some of the steps may be performed in a different order than those described below. In a manner similar to the functions and processes of FIG. 7, the functions and processes described with regard to this process also can be executed by the functional blocks in FIGS. 5 and 6, or by other functional components.

The process of forming a thermogram begins at step 800, in which the thermogram generator 66 of the analysis engine 46 receives the plurality of temperature values, which, as noted above, are graphically shown by FIG. 9A. Of course, the thermogram generator 66 typically receives those temperature values as raw data. The depiction in FIG. 9A therefore is simply for illustration purposes only.

After receiving the temperature values, the process begins calculating the temperatures between the temperature sensors 26. To that end, the process uses conventional interpolation techniques to interpolate the temperature values in a manner that produces a thermogram as noted above (step 802). Accordingly, for a thermogram of a planar thermodynamic system at steady state, the process may be considered to increase the spatial resolution of the data.

Among other ways, some embodiments may use Laplace interpolation between the temperatures observed at each temperature sensor 26. Laplace interpolation is appropriate for this function given its physical relevance—the heat equation should simplify to the Laplace equation under the assumption of steady state. The interpolant may be constructed by applying a second-order discrete finite difference Laplacian operator to the data, imposing equality conditions on the known temperatures at the sensors 26, and solving the resulting sparse linear system using an iterative solver, such as GMRES.

Figure 9B:

FIG. 9B schematically shows one example of the thermogram at this stage of the process. This figure should be contrasted with FIG. 9A, which shows a more discrete illustration of the soles of the feet 10.

Figure 9C:
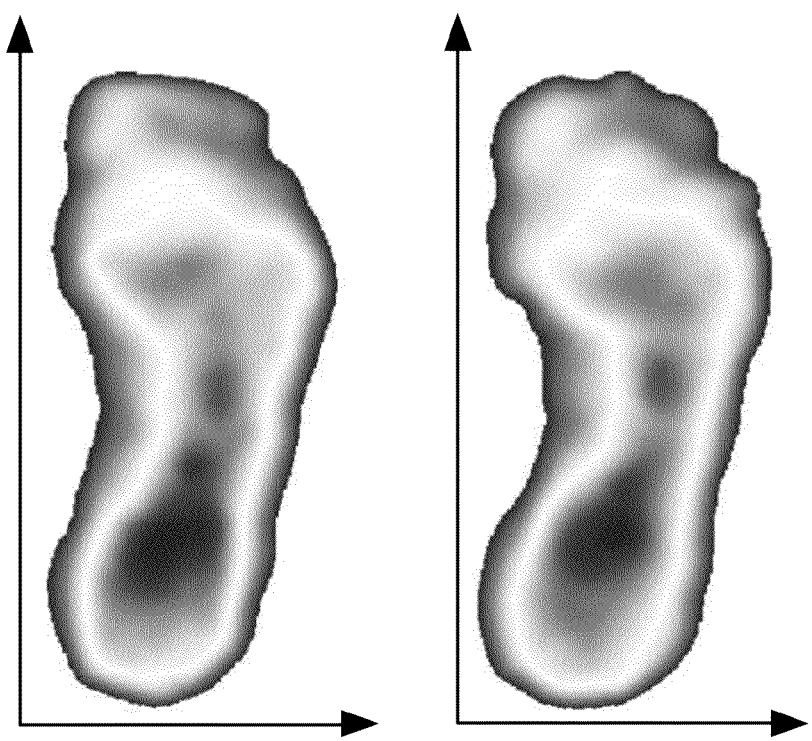

At this point, the process is considered to have formed the thermogram. For effective use, however, it nevertheless still may require further processing. Step 804 therefore orients the data/thermogram to a standard coordinate system. To that end, the process may determine the location of the sole of each foot 10, and then transform it into a standard coordinate system for comparison against other temperature measurements on the same foot 10, and on the other foot 10. This ensures that each portion of the foot 10 may be compared to itself from an earlier thermogram. FIG. 9C schematically shows one example of how this step may reorient the thermogram of FIG. 9B.

The position and orientation of the foot 10 on the platform 16 therefore is important when performing this step. For example, to determine the position and orientation of the foot 10, the analysis engine 46 and its thermogram generator 66 simply may contrast the regions of elevated temperature on the platform 16 (i.e., due to foot contact) with those at ambient temperature. Other embodiments may use pressure sensors to form a pressure map of the foot 10.

Figure 9D:
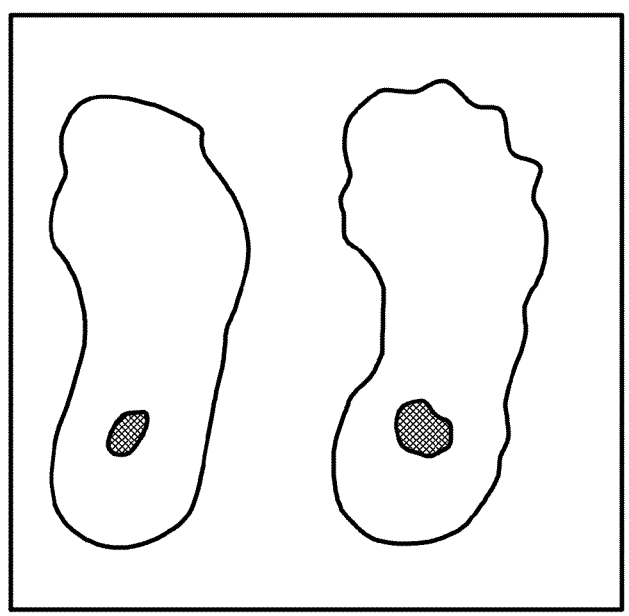

The process may end at this point, or continue to step 806, to better contrast warmer portions of the foot 10 against other portions of the foot 10. FIG. 9D schematically shows a thermogram produced in this manner from the thermogram of FIG. 9C. This figure more clearly shows two hotspots on the foot 10 than FIG. 9C. To that end, the process determines the baseline or normal temperature of the foot 10 for each location within some tolerance range. The amount to which the actual temperature of a portion of the foot 10 deviates from the baseline temperature of that portion of the foot 10 therefore is used to more readily show hotspots.

For example, if the deviation is negative, the thermogram may have some shade of blue, with a visual scale of faint blues being smaller deviations and richer blues being larger deviations. In a similar manner, positive deviations may be represented by some shade of red, with a visual scale of faint red being smaller deviations and richer reds being larger deviations. Accordingly, and this example, bright red portions of the thermogram readily show hotspots that may require immediate attention. Of course, other embodiments may use other colors or techniques for showing hotspots. Accordingly, discussion of color coding or specific colors is not intended to limit all embodiments.

Now that the thermogram generator 66 has generated the thermogram, with brighter hotspots and in an appropriate orientation, this discussion returns to FIG. 7 to determine if the thermogram presents or shows any of a number of prescribed patterns (step 704) and then analyzes any detected pattern (step 706) to determine if there are hotspots. In particular, as noted, an elevated temperature at a particular portion of the foot 10 may be indicative or predictive of the emergence and risk of a pre-ulcer 14 or ulcer 12 in the foot 10. For example, temperature deviations of about 2 degrees C. or about 4 degrees F. in certain contexts can suggest emergence of an ulcer 12 or pre-ulcer 14. Temperature deviations other than about two degrees C. also may be indicative of a pre-ulcer 14 or ulcer 12 and thus, 2 degrees C. and 4 degrees F. are discussed by example only. Accordingly, various embodiments analyze the thermogram to determine if the geography of the foot 10 presents or contains one or more of a set of prescribed patterns indicative of a pre-ulcer 14 or ulcer 12. Such embodiments may analyze the visual representation of the thermograph, or just the data otherwise used to generate and display a thermograph image—without displaying the thermograph.

A prescribed pattern may include a temperature differential over some geography or portion of the foot 10 or feet 10. To that end, various embodiments contemplate different patterns that compare at least a portion of the foot 10 against other foot data. Among other things, those comparisons may include the following:

1. A comparison of the temperature of the same portion/spot of the same foot 10 at different times (i.e., a temporal comparison of the same spot),
2. A comparison of the temperatures of corresponding portions/spots of the patient's two feet 10 at the same time or at different times, and/or
3. A comparison of the temperature of different portions/spots of the same foot 10 at the same time or at different times.

Figure 10A:
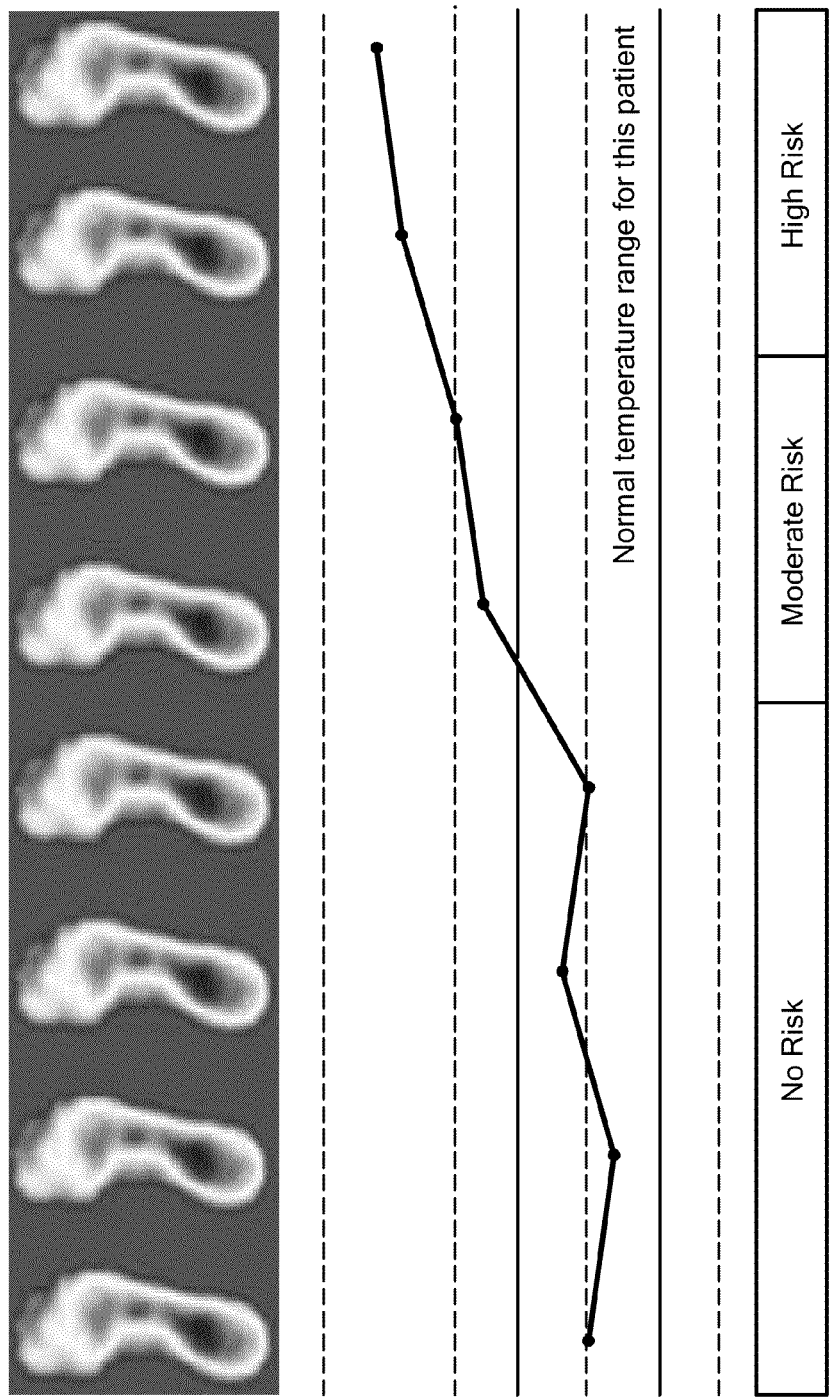
FIGS. 10A and 10B schematically show two different types of patterns that may be on the soles of a patient's foot indicating an ulcer or pre-ulcer.

As an example of the first comparison, the pattern may show a certain region of a foot 10 has a temperature that is 4 F higher than the temperature at that same region several days earlier. FIG. 10A schematically shows one example of this, in which a portion of the same foot 10—the patient's left foot 10, has a spot with an increased risk of ulceration.

Figure 10B:
Figure 10B:
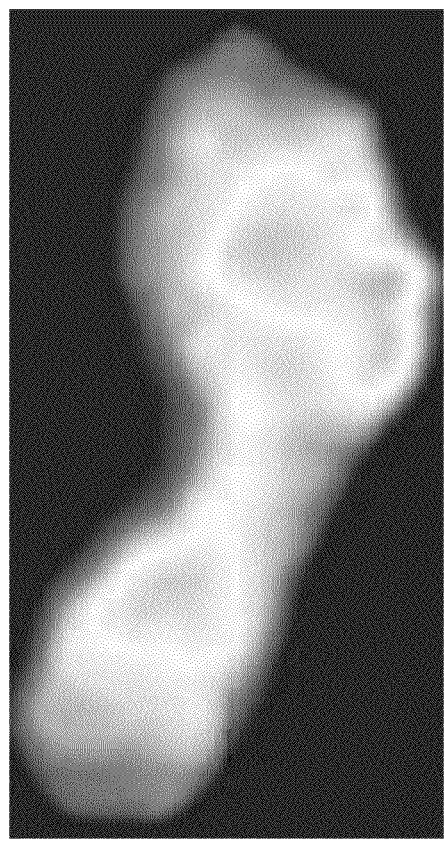

As an example of the second comparison, the pattern may show that the corresponding portions of the patient's feet 10 have a temperature differential that is 4 degrees F. FIG. 10B schematically shows an example of this, where the region of the foot 10 on the left (the right foot 10) having a black border is hotter than the corresponding region on the foot 10 on the right (the left foot 10).

As an example of the third comparison, the pattern may show localized hotspots and peaks within an otherwise normal foot 10. These peaks may be an indication of pre-ulcer 14 or ulcer 12 emergence, or increased risk of the same, which, like the other examples, alerts caregiver and patient to the need for more vigilance.

Of course, various embodiments may make similar comparisons while analyzing the thermogram for additional patterns. For example, similar to the third comparison, the pattern recognition system 68 may have a running average of the temperature of the geography of the entire foot 10 over time. For any particular spot on the foot 10, this running average may have a range between a high temperature and a low temperature. Accordingly, data indicating that the temperature at that given spot is outside of the normal range may be predictive of a pre-ulcer 14 or an ulcer 12 at that location.

Some embodiments may use machine learning and advanced filtering techniques to ascertain risks and predictions, and to make the comparisons. More specifically, advanced statistical models may be applied to estimate the current status and health of the patient's feet 10, and to make predictions about future changes in foot health. State estimation models, such as a switching Kalman filters, can process data as they become available and update their estimate of the current status of the user's feet 10 in real-time. The statistical models can combine both expert knowledge based on clinical experience, and published research (e.g., specifying which variables and factors should be included in the models) with real data gathered and analyzed from users. This permits models to be trained and optimized based on a variety of performance measures.

Models can be continually improved as additional data is gathered, and updated to reflect state-of-the-art clinical research. The models also can be designed to take into account a variety of potentially confounding factors, such as physical activity (e.g., running), environmental conditions (e.g., a cold floor), personal baselines, past injuries, predisposition to developing problems, and problems developing in other regions (e.g., a rise in temperature recorded by a sensor 26 may be due to an ulcer 12 developing in a neighboring region measured by a different sensor). In addition to using these models for delivering real-time analysis of users, they also may be used off-line to detect significant patterns in large archives of historical data. For example, a large rise above baseline temperature during a period of inactivity may precede the development of an ulcer 12.

Alternative embodiments may configure the pattern recognition system 68 and analyzer 70 to perform other processes that identify risk and emergence, as well as assist in tracking the progressions ulcers 12 and pre-ulcers 14. For example, if there is no ambient temperature data from a thermogram prior to the patient's use of the platform 16, then some embodiments may apply an Otsu filter (or other filter) first to the high resolution thermogram to identify regions with large temperature deviations from ambient. The characteristics of these regions (length, width, mean temperature, etc. . . . ) then may be statistically compared to known distributions of foot characteristics to identify and isolate feet 10. The right foot thermogram may be mirrored and an edge-alignment algorithm can be employed to standardize the data for hotspot identification.

Two conditions can be evaluated independently for hotspot identification. The first condition evaluates to true when a spatially-localized contralateral thermal asymmetry exceeds a pre-determined temperature threshold for a given duration. The second condition evaluates to true when a spatially-localized ipsilateral thermal deviation between temporally successive scans exceeds a pre-determined temperature threshold for a given duration. The appropriate durations and thermal thresholds can be determined from literature review or through application of machine learning techniques to data from observational studies. In the latter case, a support vector machine or another robust classifier can be applied to outcome data from the observational study to determine appropriate temperature thresholds and durations to achieve a desired balance between sensitivity and specificity.

Illustrative embodiments have a set of prescribed patterns against which the pattern recognition system 68 and analyzer 70 compare to determine foot health. Accordingly, discussion of specific techniques above are illustrative of any of a number of different techniques that may be used and thus, are not intended to limit all embodiments of the invention.

The output of this analysis can be processed to produce risk summaries and scores that can be displayed to various users to trigger alerts and suggest the need for intervention. Among other things, state estimation models can simulate potential changes in the user's foot 10 and assess the likelihood of complications in the future. Moreover, these models can be combined with predictive models, such as linear logistic regression models and support vector machines, which can integrate a large volume and variety of current and historical data, including significant patterns discovered during off-line analysis. This may be used to forecast whether the user is likely to develop problems within a given timeframe. The predictions of likelihood can be processed into risk scores, which also can be displayed by both users and other third parties. These scores and displays are discussed in greater detail below.

To those ends, the process continues to step 708, which generates output information relating to the health of the foot 10. Specifically, at this stage in the process, the analysis engine 46 has generated the relevant data to make a number of conclusions and assessments, in the form of output information, relating to the health of the foot 10. Among other things, those assessments may include the risk of an ulcer 12 emerging anywhere on the foot 10, or at a particular location on the foot 10. This risk may be identified on a scale from no risk to maximum risk.

Figure 11A:
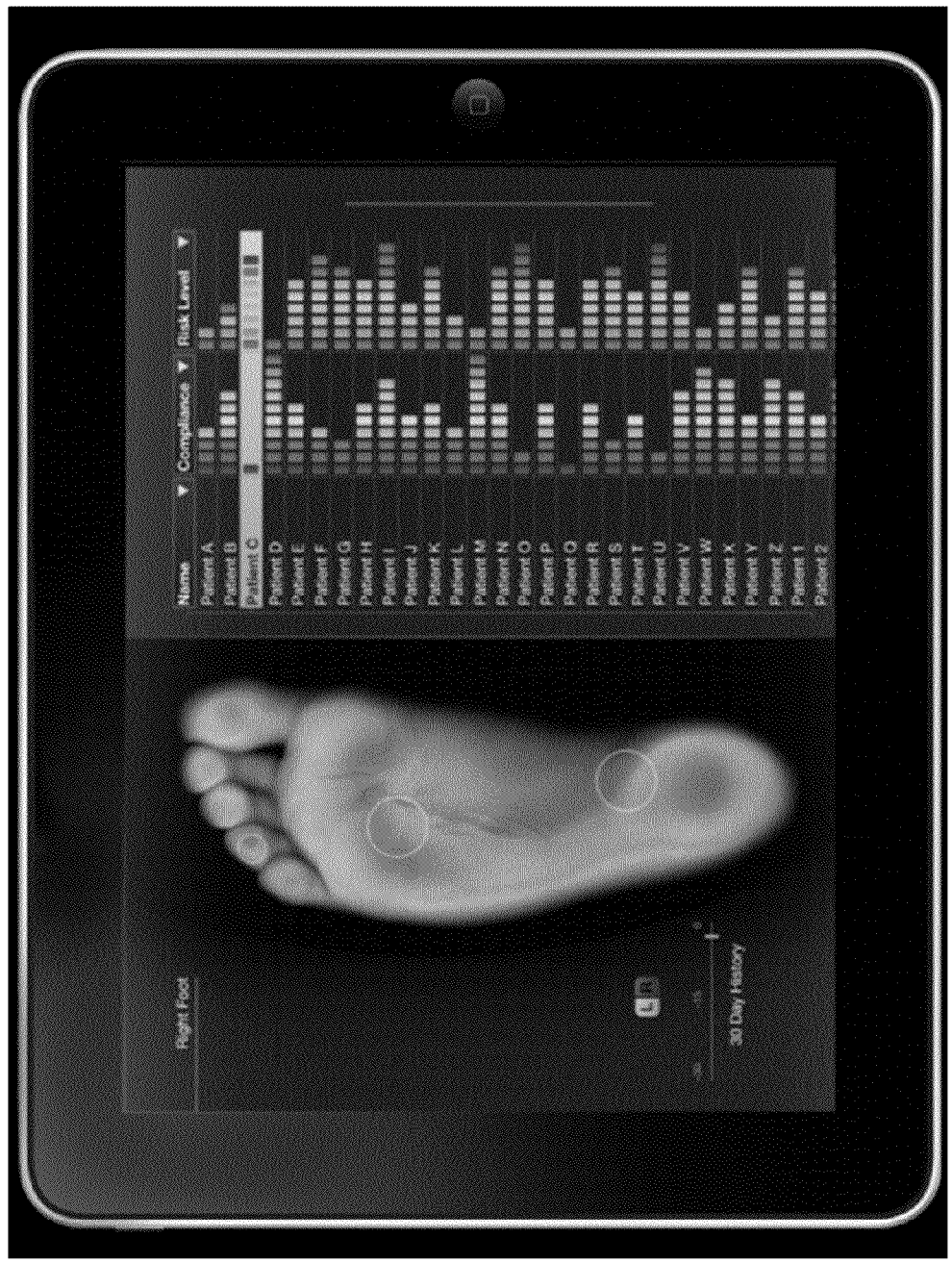
FIGS. 11A and 11B schematically show two different user interfaces that may be displayed in accordance with illustrative embodiments of the invention.
Figure 11B:
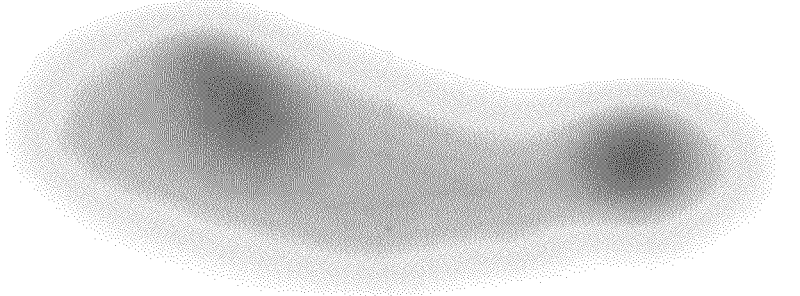

FIG. 11A shows one example of the output information in a visual format with a scale ranking the risk of ulcer emergence. The scale in this example visually displays de-identified patients (i.e., Patient A to Patient 2) as having a certain risk level of developing the foot ulcer 12. The "Risk Level" column shows one way of graphically displaying the output information, in which more rectangles indicate a higher risk of ulcer 12. Specifically, in this example, a single rectangle may indicate minimal or no risk, while rectangles filling the entire length of that table entry may indicate a maximum risk or fully emerged ulcer 12. Selection of a certain patient may produce an image of the foot 10 with a sliding bar showing the history of that patient's foot 10. FIG. 11B schematically shows a similar output table in which the risk level is characterized by a percentage from zero to hundred percent within some time frame (e.g., days). Patient C is bolded in this example due to their 80 percent risk of the emergence of an ulcer 12.

The output table thus may provide the caregiver or healthcare provider with information, such as the fact that Patient B has a 90 percent probability that he/she will develop a foot ulcer 12 in the next 4-5 days. To assist in making clinical treatment decisions, the clinician also may access the patient's history file to view the raw data.

Other embodiments produce output information indicating the emergence of a pre-ulcer 14 at some spot on the foot 10. As known by those skilled in the art, a pre-ulcer 14 may be considered to be formed when tissue in the foot 10 is no longer normal, but it has not ruptured the top layer of skin. Accordingly, a pre-ulcer 14 is internal to the foot 10. More specifically, tissue in a specific region of the foot 10 may not be receiving adequate blood supply and thus, may need more blood. When it does not receive an adequate supply of blood, it may become inflamed and subsequently, become necrotic (i.e., death of the tissue). This creates a weakness or tenderness in that region of the foot 10. Accordingly, a callous or some event may accelerate a breakdown of the tissue, which ultimately may rupture the pre-ulcer 14 to form an ulcer 12.

Illustrative embodiments may detect the emergence of a pre-ulcer 14 in any of a number of manners described above. For example, the system may compare temperature readings to those of prior thermograms, such as the running average of the temperature at a given location. This comparison may show an elevated temperature at that spot, thus signaling the emergence of a new pre-ulcer 14. In more extreme cases, this may indicate the actual emergence of a new ulcer 12.

The emergence or detection of a pre-ulcer 14 can trigger a number of other preventative treatments that may eliminate or significantly reduce the likelihood of the ultimate emergence of an ulcer 12. To that end, after learning about a pre-ulcer 14, some embodiments monitor the progression of the pre-ulcer

14. Preferably, the pre-ulcer 14 is monitored during treatment in an effort to heal the area, thus avoiding the emergence of an ulcer 12. For example, the caregiver may compare each day's thermogram to prior thermograms, thus analyzing the most up to date state of the pre-ulcer 14. In favorable circumstances, during a treatment regimen, this comparison/monitoring shows a continuous improvement of the pre-ulcer 14, indicating that the pre-ulcer 14 is healing. The output information therefore can have current and/or past data relating to the pre-ulcer 14, and the risk that it poses for the emergence of an ulcer 12.

Sometimes, patients may not even realize that they have an ulcer 12 until it has become seriously infected. For example, if the patient undesirably does not use the foot monitoring system for a long time, he/she may already have developed an ulcer 12. The patient therefore may step on the platform 16 and the platform 16 may produce output information indicating the emergence of an ulcer 12. To that end, the analyzer 70 may have prior baseline thermogram (i.e., data) relating to this patient's foot 10 (showing no ulcer), and make a comparison against that baseline data to determine the emergence of an actual ulcer 12. In cases where the data is questionable about whether it is an ulcer 12 or a pre-ulcer 14, the caregiver and/or patient nevertheless may be notified of the higher risk region of the foot 10 which, upon even a cursory visual inspection, should immediately reveal the emergence of an ulcer 12.

The process concludes at step 710, in which the process (optionally) manually or automatically notifies the relevant people about the health of the foot 10. These notifications or messages (a type of "risk message") may be in any of a number of forms, such as a telephone call, a text message, e-mail, and data transmission, or other similar mechanism. For example, the system may forward an e-mail to a healthcare provider indicating that the right foot 10 of the patient is generally healthy, while the left foot 10 has a 20 percent risk of developing an ulcer 12, and a pre-ulcer 14 also has emerged on a specified region. Armed with this information, the healthcare provider may take appropriate action, such as by directing the patient to stay off their feet 10, use specialized footwear, soak their feet 10, or immediately check into a hospital.

Accordingly, illustrative embodiments take advantage of the continuous data provided by a thermogram to ascertain various risks to foot health. In addition, such embodiments also monitor the foot 10 using an easy to follow regimen and form factor that encourages patient compliance. Early detection can assist in avoiding foot ulcers 12, while late detection can alert patients to yet undiscovered ulcers 12, which can then be effectively treated.

Various embodiments of the invention may be implemented at least in part in any conventional computer programming language. For example, some embodiments may be implemented in a procedural programming language (e.g., "C"), or in an object oriented programming language (e.g., "C++"). Other embodiments of the invention may be implemented as preprogrammed hardware elements (e.g., application specific integrated circuits, FPGAs, and digital signal processors), or other related components.

In an alternative embodiment, the disclosed apparatus and methods (e.g., see the various flow charts described above) may be implemented as a computer program product (or in a computer process) for use with a computer system. Such implementation may include a series of computer instructions fixed either on a tangible medium, such as a computer readable medium (e.g., a diskette, CD-ROM, ROM, or fixed disk) or transmittable to a computer system, via a modem or other interface device, such as a communications adapter connected to a network over a medium.

The medium may be either a tangible medium (e.g., optical or analog communications lines) or a medium implemented with wireless techniques (e.g., WIFI, microwave, infrared or other transmission techniques). The medium also may be a non-transient medium. The series of computer instructions can embody all or part of the functionality previously described herein with respect to the system. The processes described herein are merely exemplary and it is understood that various alternatives, mathematical equivalents, or derivations thereof fall within the scope of the present invention.

Those skilled in the art should appreciate that such computer instructions can be written in a number of programming languages for use with many computer architectures or operating systems. Furthermore, such instructions may be stored in any memory device, such as semiconductor, magnetic, optical or other memory devices, and may be transmitted using any communications technology, such as optical, infrared, microwave, or other transmission technologies.

Among other ways, such a computer program product may be distributed as a removable medium with accompanying printed or electronic documentation (e.g., shrink wrapped software), preloaded with a computer system (e.g., on system ROM or fixed disk), or distributed from a server or electronic bulletin board over the larger network 44 (e.g., the Internet or World Wide Web). Of course, some embodiments of the invention may be implemented as a combination of both software (e.g., a computer program product) and hardware. Still other embodiments of the invention are implemented as entirely hardware, or entirely software.

Although the above discussion discloses various exemplary embodiments of the invention, it should be apparent that those skilled in the art can make various modifications that will achieve some of the advantages of the invention without departing from the true scope of the invention.

What is claimed is:

1. A method of determining emergence of a pre-ulcer or progression of a known pre-ulcer on at least one foot of a patient, the method comprising:
   providing one or more processors;
   providing an open platform for receiving at least one foot, the open platform having a plurality of temperature sensors;
   generating, using the plurality of temperature sensors, a plurality of discrete temperature data values after receipt of the at least one foot;
   forming, by at least one of the processors, at least one thermogram of the sole of each of the at least one foot from the discrete temperature data values, the thermogram comprising a spatially continuous data set of two-dimensional temperature values across the sole;
   determining, by at least one of the processors, at any location within the at least one thermogram of the sole, whether the thermogram presents at least one of a plurality of prescribed patterns; and
   producing, by at least one of the processors, output information indicating an emergence of a pre-ulcer or progression of a known pre-ulcer in the at least one foot, producing being a function of whether the thermogram is determined to present the at least one pattern.

2. The method as defined by claim 1 further comprising:
   detecting, by at least one of the processors, a prescribed pattern on a thermogram of a portion of the at least one foot indicating the presence of a pre-ulcer on the portion; and comparing, by at least one of the processors, the thermogram of the portion of the at least one foot with data from a previous thermogram of the portion of the same foot, the previous thermogram indicating that the portion of the at least one foot is pre-ulcer free.

3. The method as defined by claim 1 further comprising:
detecting, by at least one of the processors, a prescribed pattern on a portion of the at least one foot indicating the presence of a given pre-ulcer on the portion; and
comparing, by at least one of the processors, the portion of the at least one foot with data from a previous thermogram of the portion of the same foot, the previous thermogram indicating the presence of the given pre-ulcer in that the portion of the at least one foot.

4. The method as defined by claim 1 wherein the plurality of temperature sensors are at discrete locations on the open platform corresponding to different locations of each of the at least one foot, forming comprising interpolating temperature data between at least two of the plurality of temperature sensors to produce approximate temperature readings at locations that are between the sensors.

5. The method as defined by claim 1 wherein at least one of the plurality of prescribed patterns includes a deviation in corresponding portions of the patient's two feet.

6. The method as defined by claim 1 wherein at least one of the plurality of prescribed patterns includes a deviation in one portion of the same foot over time.

7. The method as defined by claim 1 wherein the open platform comprises a floor mat.

8. The method as defined by claim 1 further comprising forwarding a data message across a network, the message having the temperature data representing the thermogram.

9. The method as defined by claim 1 wherein the the plurality of temperature sensors comprises a plurality of stationary sensors.

10. The method as defined by claim 1 where the plurality of temperature sensors comprises at least one contact sensor.

11. The method as defined by claim 1 wherein forming the thermogram comprises forming a thermogram of substantially the entirety of one of the patient's feet.

12. The method as defined by claim 1 wherein the at least one thermogram comprises a continuous data set of two-dimensional gradient values across the sole.

13. A method of determining emergence of a pre-ulcer or progression of a known pre-ulcer on at least one foot of a patient, the method comprising:
providing one or more processors;
receiving a thermogram message through a network from an open platform for receiving at least one foot, the open platform having a plurality of temperature sensors,
the plurality of temperature sensors having generated a plurality of discrete temperature data values after receipt of the at least one foot, the thermogram message including the temperature data values;
forming, by at least one of the processors, at least one thermogram of the sole of each of the at least one foot from the temperature data values, the thermogram comprising a spatially continuous data set of two-dimensional temperature values across the sole;
determining, by at least one of the processors, at any location within the at least one thermogram of the sole, whether the thermogram presents at least one of a plurality of prescribed patterns; and
producing by at least one of the processors, output information indicating an emergence of a pre-ulcer or progression of a known pre-ulcer in the at least one foot, producing being a function of whether the thermogram is determined to present the at least one pattern.

14. The method as defined by claim 13 further comprising:
detecting, by at least one of the processors, a prescribed pattern on a thermogram of a portion of the at least one foot indicating the presence of a pre-ulcer on the portion; and
comparing, by at least one of the processors, the thermogram of the portion of the at least one foot with data from a previous thermogram of the portion of the same foot, the previous thermogram indicating that the portion of the at least one foot is pre-ulcer free.

15. The method as defined by claim 13 further comprising:
detecting, by at least one of the processors, a prescribed pattern on a portion of the at least one foot indicating the presence of a given pre-ulcer on the portion; and
comparing, by at least one of the processors, the portion of the at least one foot with data from a previous thermogram of the portion of the same foot, the previous thermogram indicating the presence of the given pre-ulcer in that the portion of the at least one foot.

16. The method as defined by claim 15 wherein comparing comprises determining whether the given pre-ulcer has changed.

17. The method as defined by claim 13 wherein the plurality of temperature sensors are at discrete locations on the open platform corresponding to different locations of each of the at least one foot forming comprising interpolating temperature data between at least two of the plurality of temperature sensors to produce approximate temperature readings at locations that are between the sensors.

18. The method as defined by claim 13 wherein the open platform has a receiving area for receiving the at least one foot, the receiving area having a surface area that is greater than the surface area of the at least one foot.

19. The method as defined by claim 13 wherein at least one of the plurality of prescribed patterns shows a deviation in corresponding portions of the patient's two feet.

20. The method as defined by claim 13 wherein at least one of the plurality of prescribed patterns shows a deviation in one portion of the same foot over time.

21. The method as defined by claim 13 wherein providing an open platform comprises positioning both feet on the open platform.

22. The method as defined by claim 13 wherein the open platform comprises a floor mat.

23. An apparatus for determining emergence of a pre-ulcer or progression of a known pre-ulcer on at least one foot of a patient, the apparatus comprising:
an open platform having a plurality of temperature sensors configured to generate a plurality of discrete temperature data values after receipt of the at least one foot;
a thermogram generator operatively coupled with the open platform, the thermogram generator having a processor configured to form at least one thermogram of the sole of each of the at least one foot from the temperature data values, the thermogram comprising a spatially continuous data set of two-dimensional temperature values across the sole;
a pattern recognition system operatively coupled with the thermogram generator, the pattern recognition system configured to determine, at any location within at least one thermogram of the sole, whether the thermogram presents at least one of a plurality of prescribed patterns; and
an analyzer operatively coupled with the pattern recognition system, the analyzer being configured to produce output information indicating the emergence of a pre-ulcer or progression of a known pre-ulcer in the at least one foot as a function of whether the thermogram is determined to present the at least one pattern.

24. The apparatus as defined by claim 23 wherein the open platform comprises a floor mat.

25. The apparatus as defined by claim 23 wherein the plurality of temperature sensors comprises a plurality of stationary sensors and at least one contact sensor.

26. The apparatus as defined by claim 23 further comprising a display device for displaying indicia indicating the emergence of a pre-ulcer or progression of the known pre-ulcer in the at least one foot, the indicia being generated using the output information.

27. A computer program product for use on a computer system for determining emergence of a pre-ulcer or progression of a known pre-ulcer on at least one foot of a patient, the computer program product comprising a tangible, non-transient computer usable medium having computer readable program code thereon, the computer readable program code comprising:
program code for receiving a thermogram message through a network from an open platform for receiving at least one foot, the open platform having a plurality of temperature sensors,
the plurality of temperature sensors being configured to generate a plurality of discrete temperature data values after receipt of the at least one foot, the thermogram message including the temperature data values;
program code for forming at least one thermogram of the sole of each of the at least one foot from the temperature data values, the thermogram comprising a spatially continuous data set of two-dimensional temperature values across the sole;
program code for determining, at any location within at least one thermogram of the sole, whether the thermogram presents at least one of a plurality of prescribed patterns; and
program code for producing output information indicating the emergence of a pre-ulcer or progression of a known pre-ulcer in the at least one foot, producing being a function of whether the thermogram is determined to present the at least one pattern.

28. The computer program product as defined by claim 27 further comprising:
program code for detecting a prescribed pattern on a thermogram of a portion of the at least one foot indicating the presence of a pre-ulcer on the portion; and
program code for comparing the thermogram of the portion of the at least one foot with data from a previous thermogram of the portion of the same foot, the previous thermogram indicating that the portion of the at least one foot is pre-ulcer free.

29. The computer program product as defined by claim 27 further comprising:
program code for detecting a prescribed pattern on a portion of the at least one foot indicating the presence of a given pre-ulcer on the portion; and
program code for comparing the portion of the at least one foot with data from a previous thermogram of the portion of the same foot, the previous thermogram indicating the presence of the given pre-ulcer in that the portion of the at least one foot.

* * * * *